(12) United States Patent
Einarsson et al.

(10) Patent No.: US 7,762,973 B2
(45) Date of Patent: Jul. 27, 2010

(54) SPACER ELEMENT FOR PROSTHETIC AND ORTHOTIC DEVICES

(75) Inventors: Palmi Einarsson, San Juan Capistrano, CA (US); Arni Thor Ingimundarson, Ladera Ranch, CA (US); David Cormier, Oxnard, CA (US)

(73) Assignee: Ossur HF, Reykjavik (IS)

( * ) Notice: Subject to any disclaimer, the term of this patent is extended or adjusted under 35 U.S.C. 154(b) by 35 days.

(21) Appl. No.: 11/723,604

(22) Filed: Mar. 21, 2007

(65) Prior Publication Data
US 2007/0185425 A1 Aug. 9, 2007

Related U.S. Application Data

(63) Continuation-in-part of application No. 11/312,337, filed on Dec. 21, 2005.

(60) Provisional application No. 60/637,754, filed on Dec. 22, 2004, provisional application No. 60/739,407, filed on Nov. 25, 2005, provisional application No. 60/684,163, filed on May 25, 2005.

(51) Int. Cl.
*A61F 5/00* (2006.01)
*B32B 5/02* (2006.01)
*B32B 3/10* (2006.01)

(52) U.S. Cl. .................. 602/26; 442/99; 428/131; 428/137

(58) Field of Classification Search .................. 602/62, 602/79, 16, 23, 26; 128/882; 66/192–194, 66/196, 202; 442/99, 101, 131, 137
See application file for complete search history.

(56) References Cited

U.S. PATENT DOCUMENTS

| 937,478 | A | 10/1909 | Sims |
| 1,328,541 | A | 1/1920 | Palmer |
| 2,032,923 | A | 3/1936 | Eldridge |
| 2,717,841 | A | 9/1955 | Biefeld et al. |
| 2,935,065 | A | 5/1960 | Homier et al. |

(Continued)

FOREIGN PATENT DOCUMENTS

DE  20 2004 012892  10/2004

(Continued)

OTHER PUBLICATIONS

Article: "Thermoplastic Elastomers TPE, TPR, TPV," 6 pp., (visited Mar. 14, 2007) <<http://www.bpf.co.uk/bpfindustry/plastics_materials_thermplasrubber_TBR.cfm>>.

(Continued)

*Primary Examiner*—Patricia M Bianco
*Assistant Examiner*—Ophelia Hawthorne
(74) *Attorney, Agent, or Firm*—Bacon & Thomas, PLLC

(57) ABSTRACT

An orthotic or prosthetic spacer element including a ventilated and compressible core having first and second opposed surfaces, and a discrete and continuous web-like silicone-based frictional layer secured to the core first surface. The frictional layer and the core first surface have a plurality of coinciding apertures formed in a pattern. The spacer element may include a foam layer secured to the core second surface such that the foam layer and the core have different rigidities. A layer of hook-receivable material may be directly or indirectly secured to the second core surface.

26 Claims, 25 Drawing Sheets

U.S. PATENT DOCUMENTS

| | | | |
|---|---|---|---|
| 3,089,486 A | 5/1963 | Pike | |
| 3,463,147 A | 8/1969 | Stubbs | |
| 3,514,313 A | 5/1970 | Martel et al. | |
| 3,520,765 A | 7/1970 | Bateman | |
| 3,561,436 A | 2/1971 | Gaylord, Jr. | |
| 3,789,842 A | 2/1974 | Froimson | |
| 3,877,426 A | 4/1975 | Nirschl | |
| 3,916,077 A | 10/1975 | Damrau | |
| 4,193,395 A | 3/1980 | Gruber | |
| 4,204,532 A | 5/1980 | Lind et al. | |
| 4,269,179 A | 5/1981 | Burton et al. | |
| 4,291,072 A | 9/1981 | Barrett et al. | |
| 4,336,279 A | 6/1982 | Metzger | |
| 4,396,012 A | 8/1983 | Cobiski | |
| 4,472,461 A | 9/1984 | Johnson | |
| 4,782,605 A * | 11/1988 | Chapnick | 36/44 |
| 4,856,502 A | 8/1989 | Ersfeld et al. | |
| 4,922,929 A | 5/1990 | DeJournett | |
| 4,989,593 A | 2/1991 | Campagna et al. | |
| 4,991,574 A * | 2/1991 | Pocknell | 602/48 |
| 5,154,682 A * | 10/1992 | Kellerman | 36/44 |
| 5,322,729 A | 6/1994 | Heeter et al. | |
| 5,468,219 A | 11/1995 | Crippen | |
| 5,497,513 A | 3/1996 | Arabeyre et al. | |
| 5,540,982 A | 7/1996 | Scholz et al. | |
| 5,635,201 A | 6/1997 | Fabo | |
| 5,769,808 A | 6/1998 | Matthijs et al. | |
| 5,774,902 A * | 7/1998 | Gehse | 2/458 |
| 5,865,776 A | 2/1999 | Springs | |
| 5,916,187 A | 6/1999 | Brill | |
| 5,948,707 A | 9/1999 | Crawley et al. | |
| 5,971,946 A | 10/1999 | Quinn | |
| 6,022,617 A | 2/2000 | Calkins | |
| 6,402,713 B1 | 6/2002 | Doyle | |
| 6,405,731 B1 | 6/2002 | Chiang | |
| 6,543,158 B2 * | 4/2003 | Dieckhaus | 36/44 |
| 6,592,539 B1 * | 7/2003 | Einarsson et al. | 602/62 |
| 6,656,142 B1 | 12/2003 | Lee | |
| 6,726,641 B2 * | 4/2004 | Chiang et al. | 602/5 |
| 6,861,379 B1 * | 3/2005 | Blaszczykiewicz | 442/373 |
| D519,637 S | 4/2006 | Nordt et al. | |
| D519,638 S | 4/2006 | Nordt et al. | |
| D520,141 S | 5/2006 | Nordt et al. | |
| D521,644 S | 5/2006 | Nordt et al. | |
| 7,169,720 B2 * | 1/2007 | Etchells et al. | 442/239 |
| 7,303,539 B2 * | 12/2007 | Binder et al. | 602/75 |
| 2002/0132086 A1 | 9/2002 | Su-Tuan | |
| 2004/0058102 A1 * | 3/2004 | Baychar | 428/34.1 |
| 2006/0015980 A1 | 1/2006 | Nordt, III et al. | |
| 2006/0020237 A1 | 1/2006 | Nordt, III et al. | |
| 2006/0026732 A1 | 2/2006 | Nordt, III et al. | |
| 2006/0026733 A1 | 2/2006 | Nordt, III et al. | |
| 2006/0026733 A1 | 2/2006 | Nordt, III et al. | |
| 2006/0026736 A1 | 2/2006 | Nordt, III et al. | |
| 2006/0030802 A1 | 2/2006 | Nordt, III et al. | |
| 2006/0030803 A1 | 2/2006 | Nordt, III et al. | |
| 2006/0030804 A1 | 2/2006 | Nordt, III et al. | |
| 2006/0030805 A1 | 2/2006 | Nordt, III et al. | |
| 2006/0030806 A1 | 2/2006 | Nordt, III et al. | |
| 2006/0070164 A1 | 4/2006 | Nordt, III et al. | |
| 2006/0070165 A1 | 4/2006 | Nordt, III et al. | |

FOREIGN PATENT DOCUMENTS

| | | |
|---|---|---|
| EP | 0 611 069 A | 8/1994 |
| WO | WO 00/70984 | 11/2000 |

OTHER PUBLICATIONS

Advertisement: "Custom Engineered Fabrics and Products for Advanced High Performance," 1p., Gehring Textiles (vistied Dec. 15, 2005) <<http://www.gehringtextiles.com/d3.html>>.

\* cited by examiner

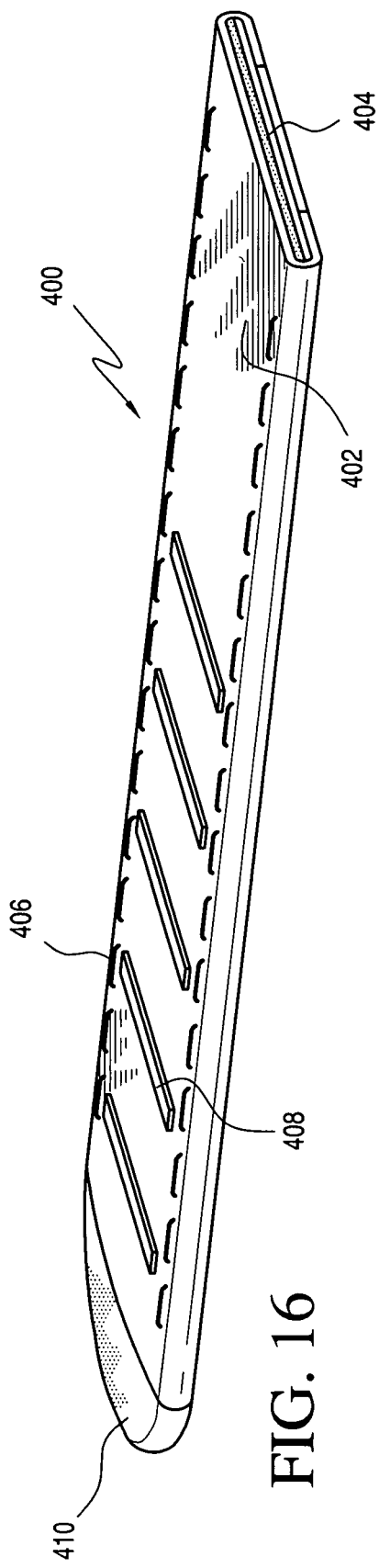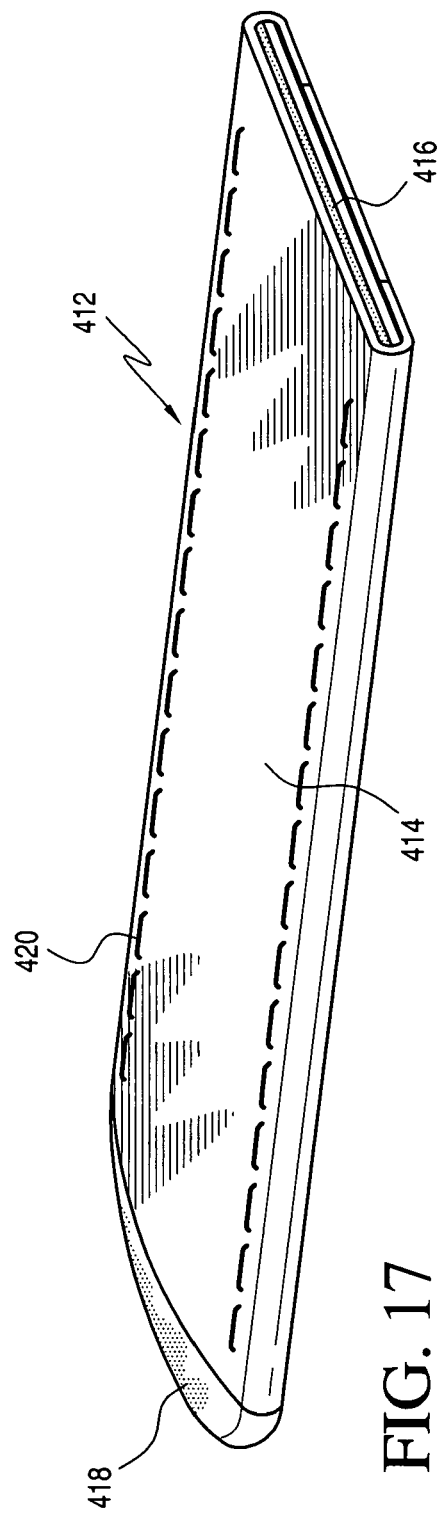
FIG. 16
FIG. 17

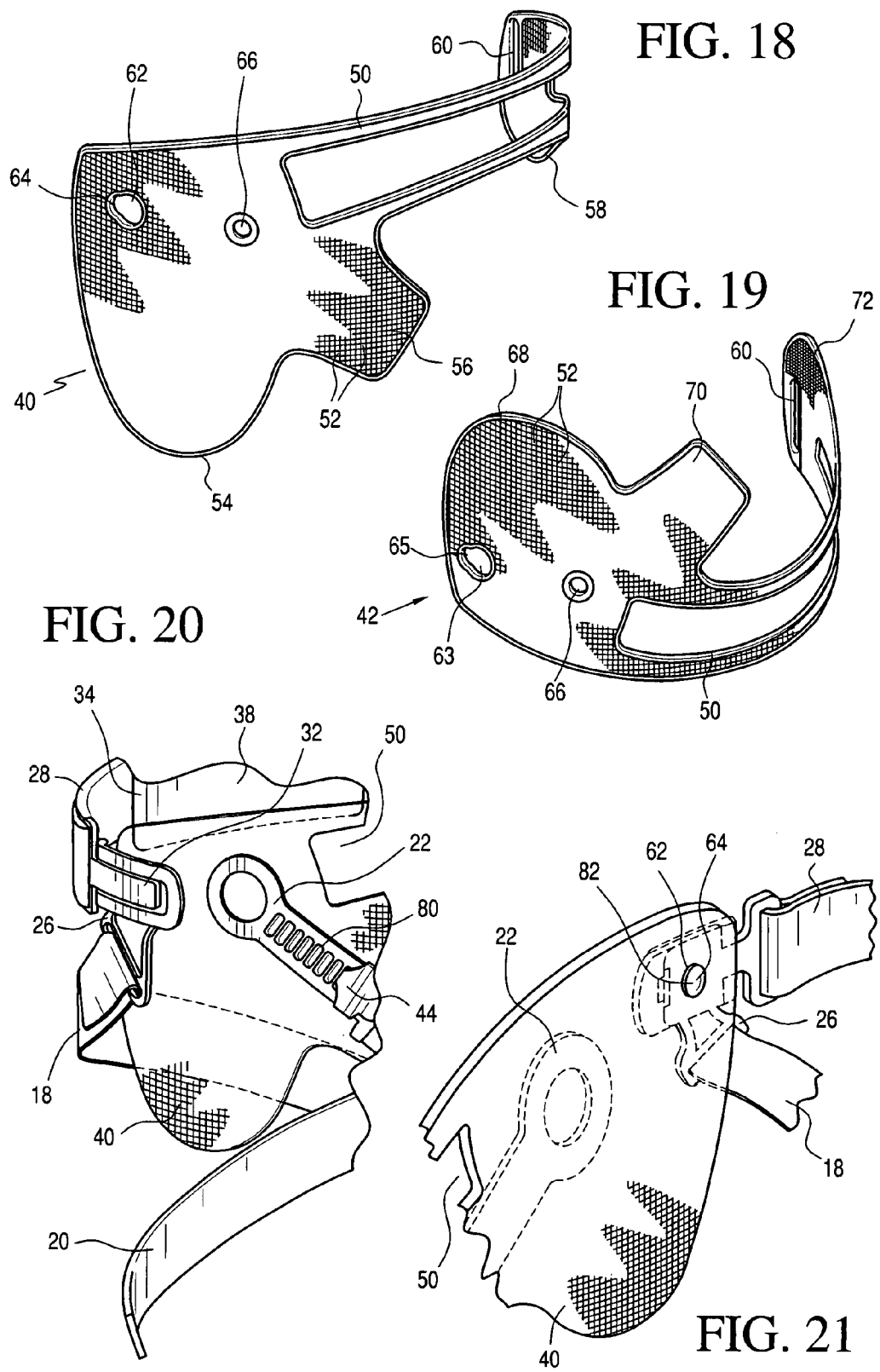

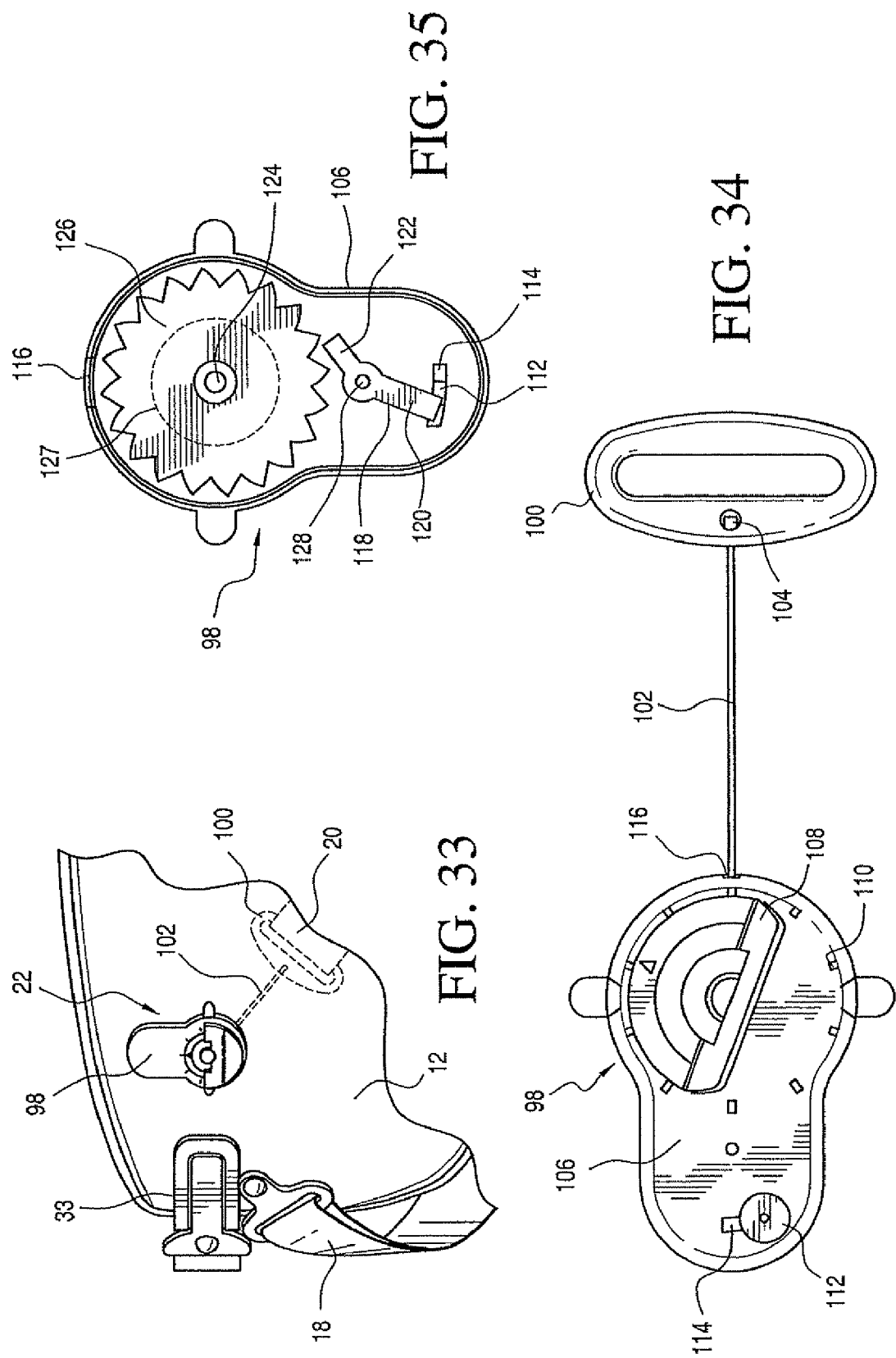

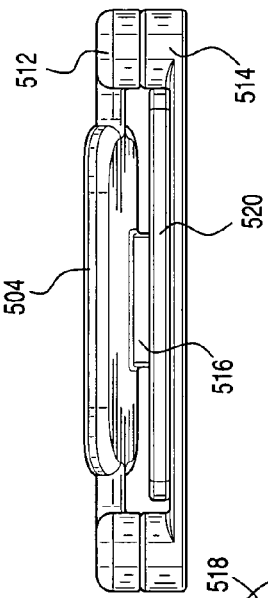
FIG. 40
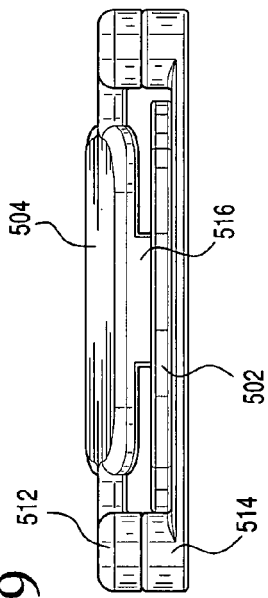
FIG. 39
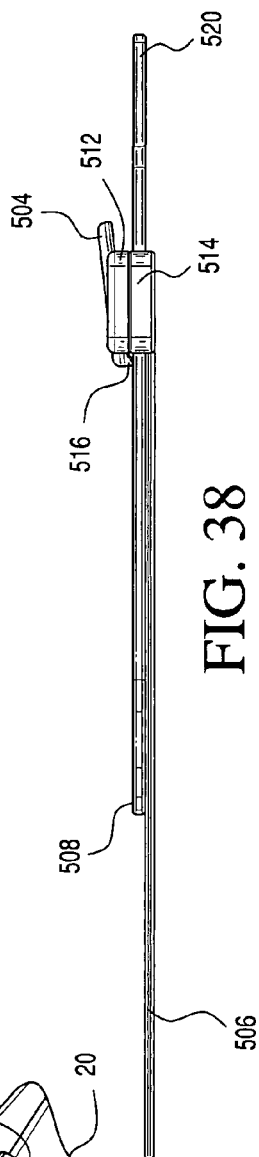
FIG. 38
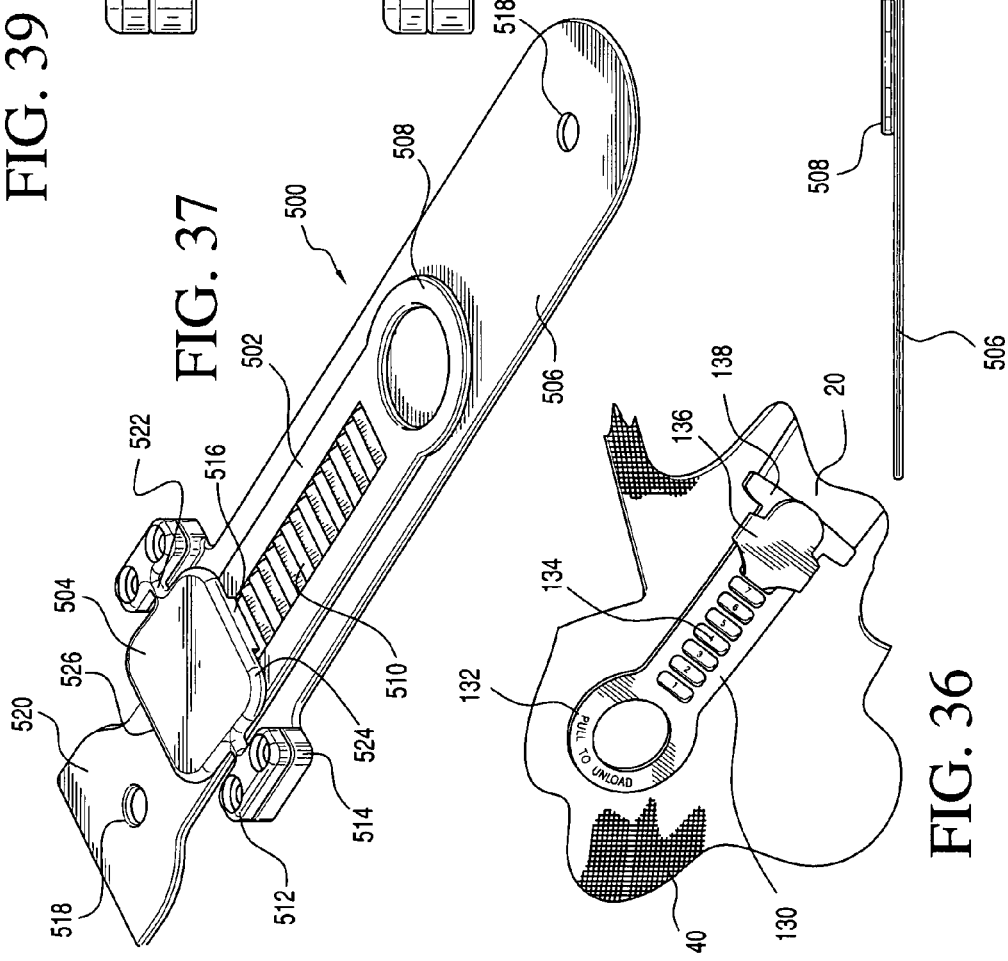
FIG. 37
FIG. 36

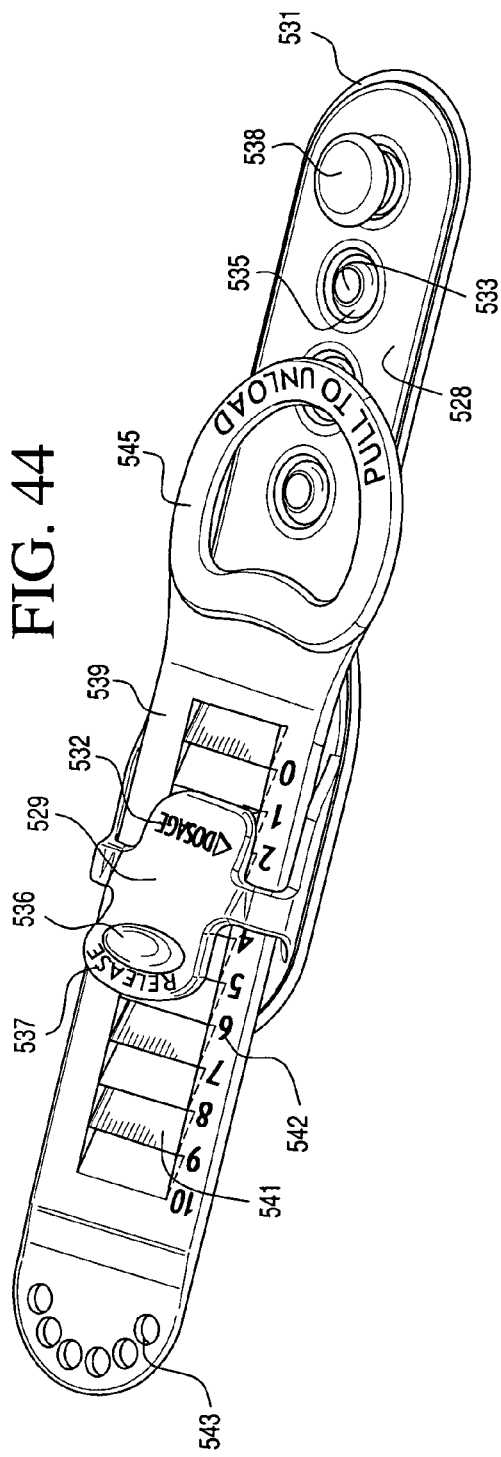
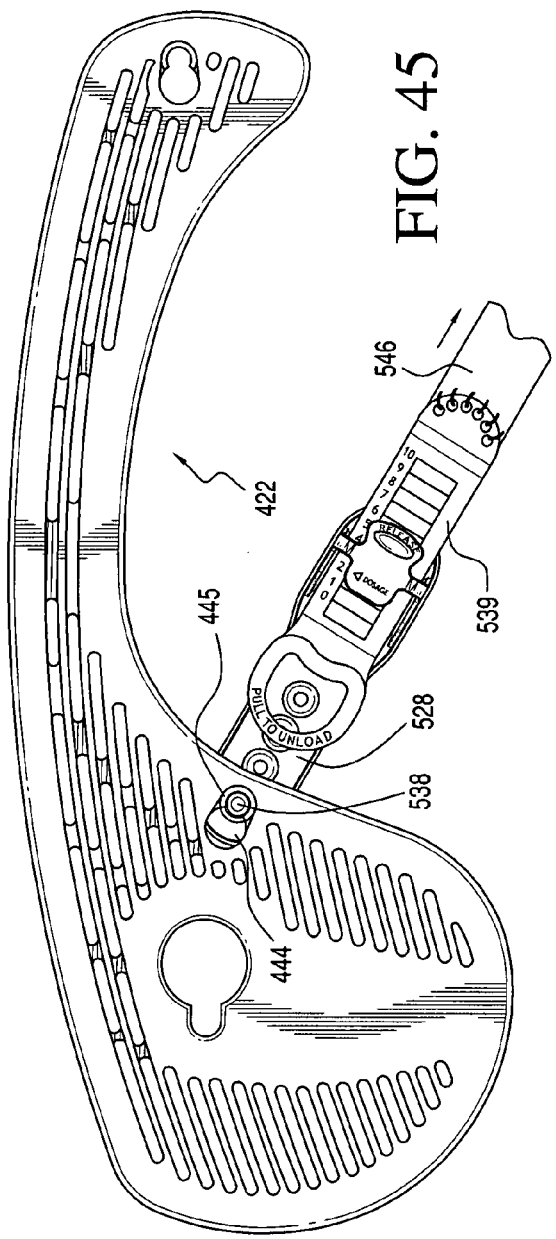
FIG. 44
FIG. 45

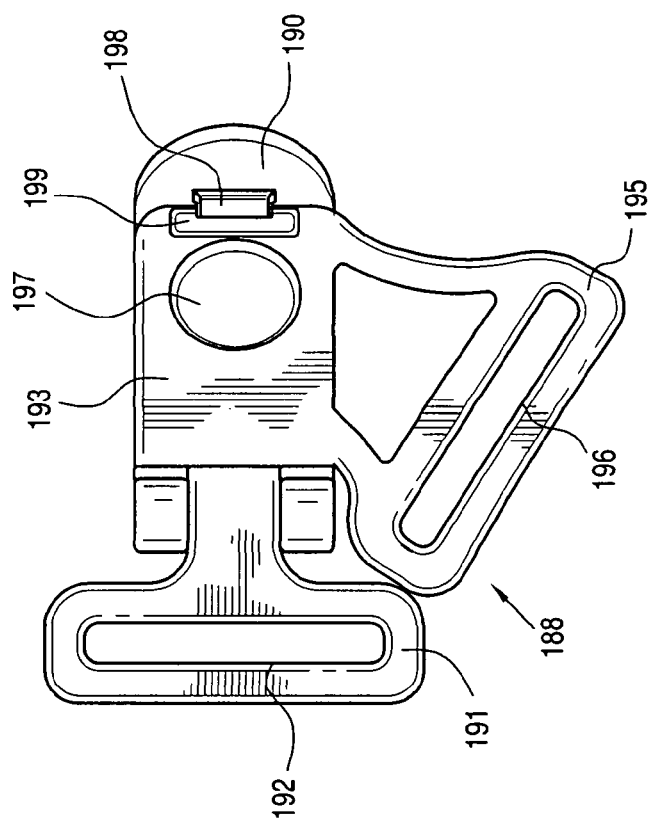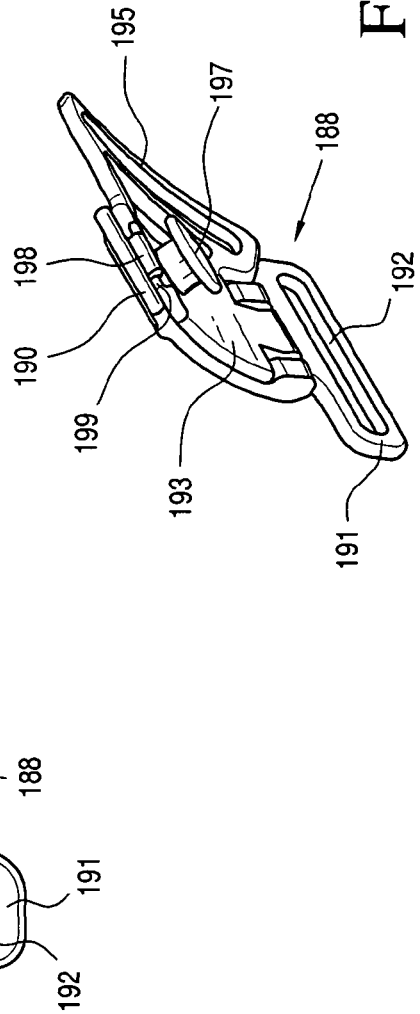

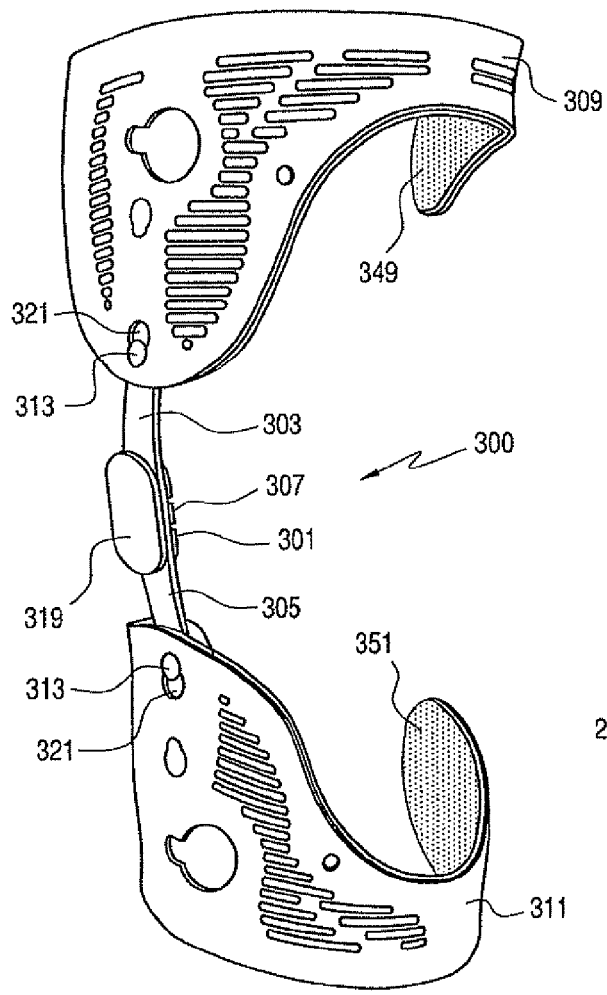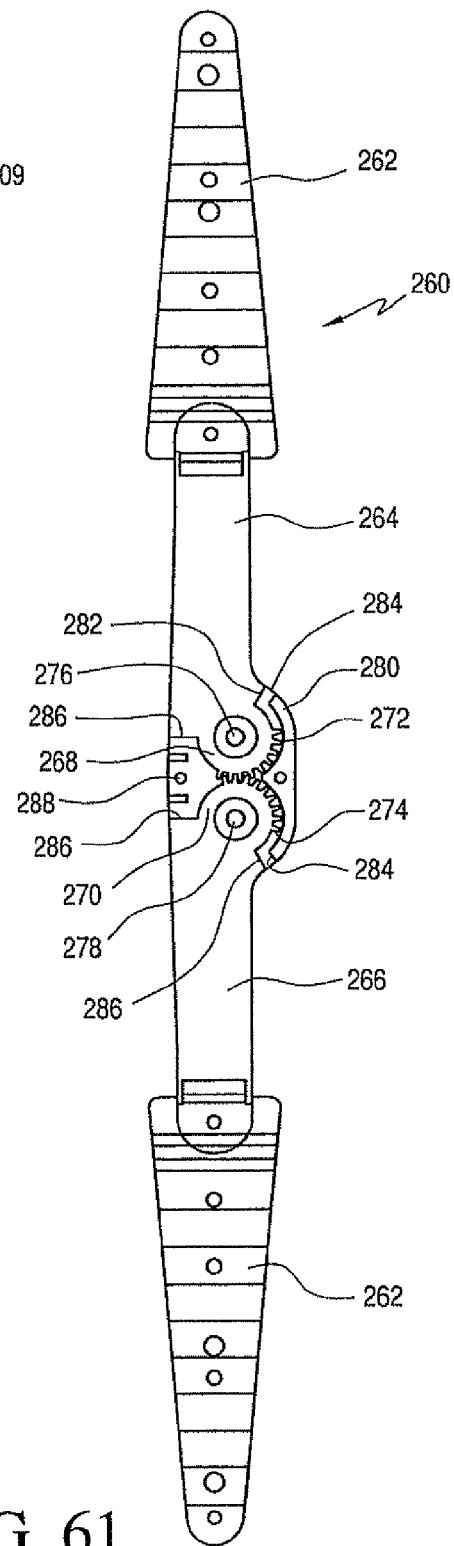
FIG. 60
FIG. 61

SPACER ELEMENT FOR PROSTHETIC AND ORTHOTIC DEVICES

CROSS REFERENCE TO RELATED APPLICATIONS

This application is a continuation-in-part of U.S. application Ser. No. 11/312,337 filed on Dec. 21, 2005 which claims the benefit of U.S. provisional application Nos. 60/637,754 filed Dec. 22, 2004, 60/684,163 filed May 25, 2005, and 60/739,407 filed Nov. 25, 2005.

BACKGROUND

A. Background Information on Knee Braces

Knee braces are widely used to treat a variety of knee infirmities. Such braces may be configured to impart forces or leverage on the limbs surrounding the knee joint in order to relieve compressive forces within a portion of the knee joint, or to reduce the load on that portion of the knee. Moreover, in the event that knee ligaments are weak and infirm, a knee brace may stabilize, protect, support, or rehabilitate the knee.

The knee is acknowledged as one of the weakest joints in the body, and serves as the articulating joint between the thigh and calf muscle groups. The knee is held together primarily by small but powerful ligaments. Knee instability arising out of cartilage damage, ligament strain and other causes is relatively commonplace since the knee joint is subjected to significant loads during the course of almost any kind of physical activity requiring the use of the legs.

A healthy knee has an even distribution of pressure in both the medial and lateral compartments of the knee. It is normal for a person with a healthy knee to place a varus moment on the knee when standing so that the pressure between the medial and lateral compartments is uneven but still natural.

One type of knee infirmity that many individuals are prone to having is compartmental osteoarthritis. Compartmental osteoarthritis may arise when there is a persistent uneven distribution of pressure in one of the medial and lateral compartments of the knee. Compartmental osteoarthritis can be caused by injury, obesity, misalignment of the knee, or simply due to aging of the knee.

A major problem resulting from osteoarthritis of the knee is that the smooth cartilage lining the inside of the knee wears away. This leads to a narrowing of the joint space with the development of cysts and erosions in the bone ends. Because of the narrowing of the joint, bone comes directly in contact with bone, and an uneven distribution of pressure develops across the knee which may result in the formation of bone spurs around the joint. All of these changes ultimately lead to increasing pain and stiffness of the joint.

While there are no cures to osteoarthritis, there are many treatments. Individuals who have a diagnosis of isolated medial compartmental osteoarthritis of the knee are confronted with a variety of treatment options such as medications, surgery, and nonsurgical interventions. Nonsurgical interventions include the use of canes, lateral shoe wedges, and knee bracing.

Knee bracing is useful to provide compartment pain relief by reducing the load on the compartment through the application of an opposing external valgus or varus moment about the knee joint. Unloading knee braces have been shown to significantly reduce osteoarthritis knee pain while improving knee function.

B. Prior Art Knee Braces

There are many known unloading knee braces. An example of a known brace is described in U.S. Pat. No. 5,277,698 assigned to Generation II Orthotics, Inc. of British Columbia, which is incorporated herein by reference. Typically, braces of this type are designed to apply a moment about the knee through two mechanisms. The first mechanism is through the angulations of hinge components which induce a bending moment at a hinge. The second mechanism is provided by a three-point bending system via a force strap that spirals around the knee and applies a force to a prescribed aspect of the knee.

FIGS. 1 and 2 exemplify the application of forces by the brace on a leg and over a knee joint according to U.S. Pat. No. 5,277,698. The arrows $B_1$ and $B_2$ show lateral and force strap forces. The resulting moments in the leg due to lateral forces are shown by arrows $Y_1$ and $Y_2$. The principal force A is that applied immediately adjacent that compartment of the knee having osteoarthritis. FIG. 2 shows R as the normal axis of rotation of the knee. The resultant moment $Y_R$ is a single rotational moment.

It has been found that as the force strap is increased in tension, the hinge valgus producing moment decreases. Therefore, the force strap and the hinge are found not to be adequately working in harmony. More specifically, it was discovered that the hinge produces about 20% of the total valgus moment in this brace. It is believed that since the hinge is aligned close to the knee, the strap urges the knee against the hinge. Moreover, the rigidity of this type of hinge limits the displacement of the hinge relative to the knee.

In a conventional brace having a hinge, a clearance is provided between the hinge and the knee to allow for movement of the knee towards the hinge. This results in a bulky brace since a large hinge is required which may extend at least an inch away from the knee.

It has been determined that if more unloading of the knee is required by the brace than is obtained from normal strap tension, and if the force strap is further tightened, the knee is drawn towards the hinge and might strike the hinge. This results in the hinge applying forces to the knee that counteract the force applied by the force strap. In turn, the additional tightening of the force strap is mitigated or negated by the force exerted onto the knee from the hinge.

For example, a study was conducted on a patient wearing a conventional knee brace having a force strap. In normal strap tension, the force strap component unloaded 5.8 Nm of the knee and the hinge unloaded about 2.2 Nm. By increasing the force strap tension, the unloading of the force strap resulted in 11.6 Nm, but the hinge resulted in unloading −2.4 Nm since the hinge was pressed against the knee.

As will be more fully evident in the ensuing discussion, the embodiments described herein are provided to overcome the deficiencies of prior art unloading braces by including arrangements that provide maximum unloading of the knee brace, while removing the mitigating effects of the hinges in known knee braces. Moreover, the embodiments of the invention are arranged for treating compartmental osteoarthritis, and have improved mechanical properties that remove undesirable rotational forces incurred by the brace and provide a more effective mechanism for generating a valgus or varus moment at the knee.

While known knee braces are successful at reducing pain at or stabilizing a knee joint, many users find these braces to be bulky, difficult to don, complicated to configure, and uncomfortable to wear. For these reasons, the embodiments described herein have streamlined features capable of providing relief for medial or lateral compartmental osteoarthritis, or functional stability of the knee without the attendant drawbacks of known unloading knee braces.

SUMMARY

Embodiments of the present invention are described in connection to an improved knee brace and knee bracing method that serve to reduce the effects of either medial compartmental or lateral compartmental osteoarthritis. Embodiments of the knee brace and variations of the knee bracing method reduce the effects of compartmental osteoarthritis by applying multiple forces to the knee on the side remote from the compartment having osteoarthritis while providing forces on the side of the compartment to maintain the brace securely on a leg while minimizing rotational forces. The embodiments of the features described herein are not limited to usage in a knee brace, and may be extended to a variety of orthopedic and prosthetic applications.

According to one embodiment, the knee brace is provided with at least one breathable spacer element having an inner surface connected to an inner facing surface of at least one of the proximal and distal members. The spacer element defines an outer surface opposing the inner surface and includes a frictional feature or layer.

While described herein in the exemplary embodiment of a knee brace, the spacer element described herein may be used in a variety of prosthetic or orthotic applications. In particular, the spacer element may be provided without any relationship to a particular prosthetic or orthotic device, and used in a variety of applications where frictional control, breathability, compression or padding is required or desirable.

In one embodiment of the spacer element, both the spacer element and the frictional feature are perforated. According to this embodiment, the spacer element is a textile having a surface with a plurality of apertures upon which a discrete and continuous web-like silicone frictional layer is secured. This yields a breathable and compressible spacer element that provides frictional resistance to forces exerted thereon.

For example, this spacer element may be used in combination with the knee brace embodiments described herein so as to prevent rotation of the knee brace on the leg of the wearer. Moreover, by providing the spacer element on both proximal and distal portions of the knee brace prevents the proximal and distal portions of the knee brace from drawing closer to one another due to the forces applied by the force straps.

In another embodiment of the spacer element, a foam (or similar compressible material) layer is secured to the core along a surface opposite to the surface with the frictional layer. The foam layer preferably has a different rigidity than a rigidity of the textile core. In variations of this embodiment, additional layers of foam (or similar compressible materials) may be used having different rigidities.

In yet another embodiment of the spacer element, a hook-receivable material may be secured to the core on a side opposite to the side with the frictional layer.

In variations of the frictional layer, the frictional layer includes a plurality of apertures that correspond to apertures of the core. In alternative variation, the frictional layer includes a plurality of apertures that are independent of apertures defined by the core. In such a variation, the frictional layer does not prevent breathability of the core.

In yet another variation of the frictional layer, the frictional layer may include areas having different thicknesses. The different thicknesses may be formed by molding, laminating or coating the frictional layer so as to form different thickness regions, or alternatively, the frictional layer may comprise different layers located at specific areas to obtain the different thicknesses. Furthermore, the frictional layer may include areas having different hardness properties relative to other areas.

In combination with the force straps and spacer elements of the knee brace described herein, one can achieve more unloading forces than with one force strap without increasing the pressure applied to the knee. This is due to the total unloading moment that is doubled with two force straps; the same amount of pressure is applied to the knee since there are two pressure points.

Second proximal and distal principal points of force are generated by the spacer elements secured to the frame members on a second side of the leg at locations above and below, respectively, the first proximal and distal principal points of force. The spacer elements maintain the knee brace on a leg and the frame members apart. The spacer elements may remove the need for a hinge as is used in the prior art braces.

Of course, the spacer elements are only exemplified herein in combination with a knee brace. However, the spacer elements may be used in a variety of orthopedic, prosthetic and other applications beyond just knee braces where frictional control, breathability, compression or padding is required or desirable.

Of course, other methods, embodiments, and variations thereof are described in greater detail in the following discussion.

BRIEF DESCRIPTION OF THE DRAWINGS

These and other features, aspects, and advantages of the present invention will become better understood with regard to the following description, appended claims, and accompanying drawings where:

FIGS. 11 and 12 are perspective views of a variation of the force strap and the stability strap, respectively.

FIG. 18 is a detailed perspective view of the proximal shell of FIG. 11.

FIG. 19 is a detailed perspective view of the distal shell of FIG. 11.

FIG. 20 is a detailed sectional view of cut-away XX-XX in FIG. 11.

FIG. 21 is a detailed section view of FIG. 20 generally rotated about 180°.

FIG. 33 is a perspective view of a variation of a tightening device on an embodiment of the knee brace.

FIG. 34 is a plan view of the tightening device according to FIG. 33.

FIG. 35 is a schematic plan view of the tightening device according to FIG. 33.

FIG. 36 is a perspective view of another variation of a tightening device on an embodiment of the knee brace.

FIG. 37 is a perspective view of yet another variation of a tightening device.

FIG. 38 is an elevational view of the tightening device of FIG. 37.

FIG. 39 is a rear elevational view of the tightening device of FIG. 37.

FIG. 40 is a front elevational view of the tightening device of FIG. 37.

FIG. 44 is perspective view of another variation of a tightening device including the base in FIG. 41.

FIG. 45 is a perspective view of the tightening device according to FIG. 44 secured onto the shell of FIG. 22.

FIG. 56 is top plan view of another variation of a buckle assembly.

FIG. 57 is a bottom plan view of FIG. 56.

FIG. 58 is perspective view of the buckle assembly of FIG. 56.

FIG. 60 is a schematic perspective view of another embodiment of the knee brace.

FIG. 61 is an elevational view of a variation of a hinge for the knee brace.

DETAILED DESCRIPTION OF VARIOUS EMBODIMENTS

A. Overview

Figure 2:
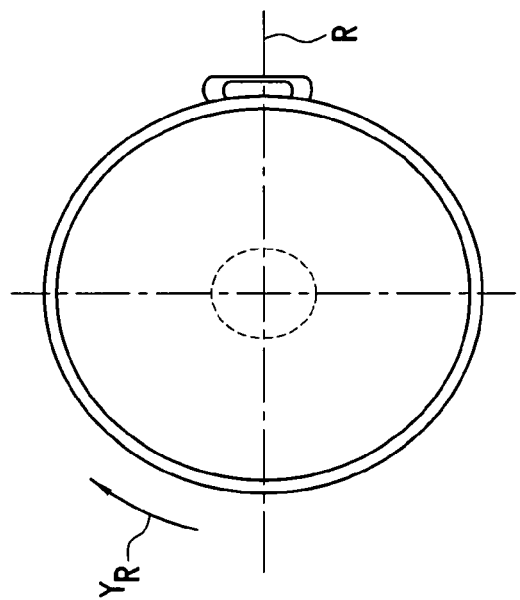
FIG. 2 illustrates the rotational force applied on a leg by the prior art knee brace of FIG. 1.

A better understanding of different embodiments of the invention may be had from the following description read in conjunction with the accompanying drawings in which like reference characters refer to like elements.

While the disclosure is susceptible to various modifications and alternative constructions, certain illustrative embodiments are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. § 112, paragraph 6.

B. Environment and Context of Embodiments

Numerous embodiments of the invention are provided to reduce the effect of osteoarthritis in a knee joint, or stabilize a knee joint that has been weakened by injury or other infirmities. Embodiments of the invention may be configured to reduce or cure both medial and lateral knee joint infirmities.

Embodiments of the invention are particularly adapted for a human knee joint, and may be dimensioned to accommodate different types, shapes and sizes of human joints and appendages. In addition, embodiments may be modified to orient principal forces exerted by strap systems of the embodiments at any desirable location to treat knee infirmities.

For explanatory purposes, each knee brace embodiment described herein is divided into sections which are denoted by general anatomical terms for the human body. Each of these terms is used in reference to a human leg which is divided in similar sections with a proximal-distal plane generally extending along the meniscus of the knee between the femur and tibia.

Figure 3:
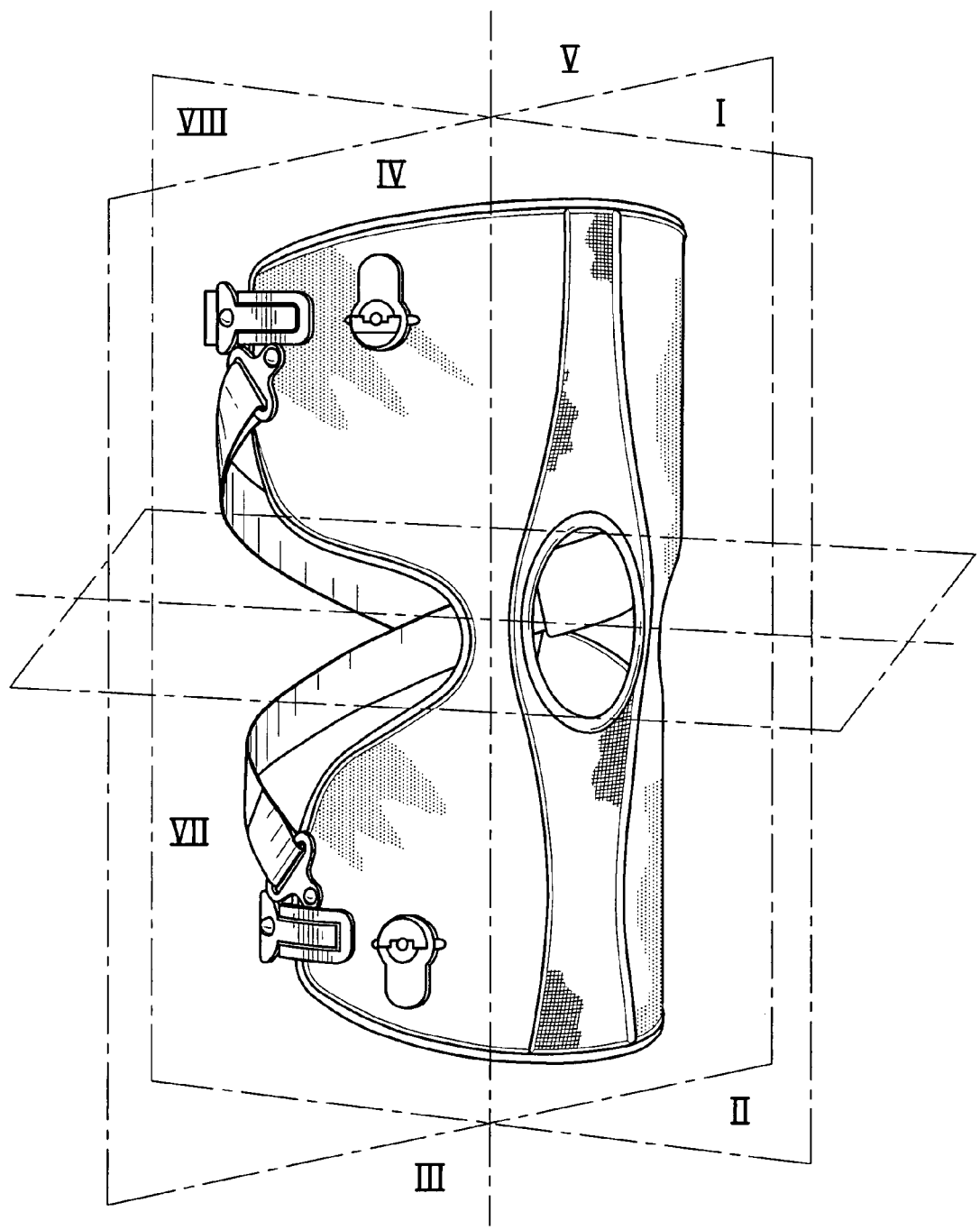
FIG. 3 is a perspective view of an embodiment of a knee brace divided along anterior-posterior, proximal-distal, and lateral-medial planes.

In reference to FIG. 3, an embodiment of the knee brace is divided into anterior and posterior sections by an anterior-posterior plane. The anterior-posterior plane generally corresponds to the coronal or frontal plane of a human leg. Each of the anterior and posterior sections is further divided about the center of the knee by a transverse or proximal-distal planes, and median, sagittal or lateral-medial plane.

Figure 4:
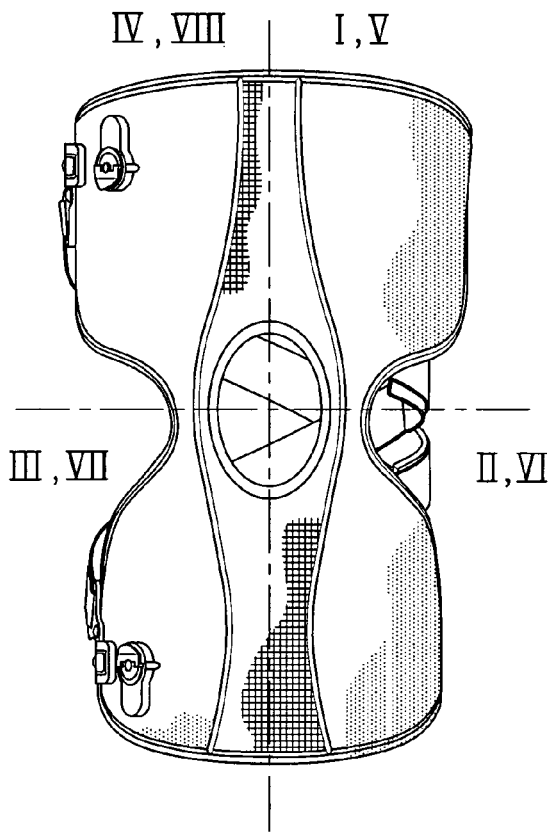
FIG. 4 is a front elevation view of the embodiment of FIG. 3 divided along the lateral-medial and proximal-distal planes.
Figure 5:
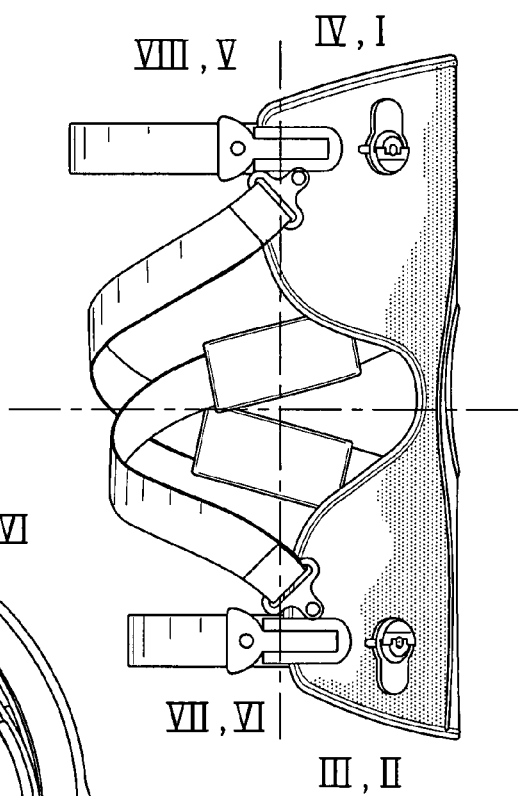
FIG. 5 is a side elevation view of the embodiment of FIG. 3 divided along the anterior-posterior and proximal-distal planes.
Figure 6:
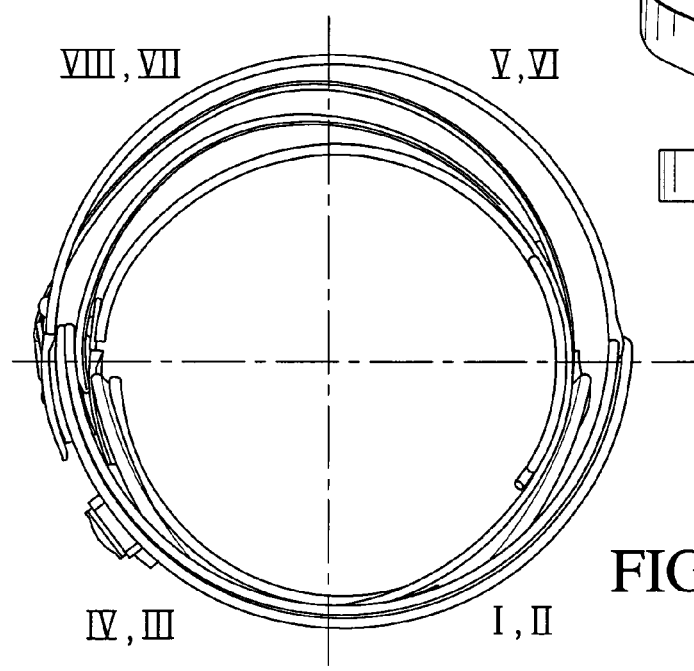
FIG. 6 is a top plan view of the embodiment of FIG. 3, divided along the anterior-posterior and lateral-medial planes.

Referring specifically to FIGS. 4-6, the anterior section of the knee brace of FIG. 3 has the following quadrants: (I) proximal-medial, (II) distal-medial, (III) distal-lateral, and (IV) proximal-lateral. The posterior section of the knee brace of FIG. 3 has the following quadrants: (V) proximal-medial, (VI) distal-medial, (VII) distal-lateral, and (VIII) proximal-lateral.

The anatomical terms described herein are not intended to detract from the normal understanding of such terms as readily understood by one of ordinary skill in the art of orthotics.

C. Various Embodiments of the Knee Brace i. Overview of Knee Brace Embodiments

Referring to FIGS. 7-10, a knee brace embodiment 10 is shown. While this knee brace is particularly shown and configured for treating lateral osteoarthritis of the knee, it is understood that the knee brace may be configured by reversing the features in order to treat medial osteoarthritis of the knee.

According to this embodiment, the brace 10 includes a sleeve 12 covering or upon which various components and assemblies are secured. As will be described below in reference to proximal and distal frame elements or shells 40, 42, these shells are connected to, inserted into, or secured against the sleeve to provide sufficient rigidity to the brace.

According to this embodiment, the sleeve 12 includes a breathable central strip portion 14 generally extending along the proximal-distal plane of the brace 10, and a center ring 16 located approximately about the center of the sleeve 12. The center ring 16 is preferably constructed from an elastic material so as to provide sufficient flexure of the brace 10 about the center portion thereof, and is located so as to assist a user of the device in placing the center portion over the anterior knee. Moreover, the portion of the sleeve 12 corresponding to the proximal portion of the knee is left exposed in order prevent interference of extension and flexion of the knee.

First and second force straps 18, 20 are each secured at a first end to a corresponding tightening device 22, 23 that protrudes out of an opening 24, 25 of the sleeve 12. The second end of each of the force straps 18, 20 is secured to a corresponding bracket assembly 26, 27 also secured to the sleeve 12. The first and second force straps 18, 20 intersect at intersection point 21 that is located near or along the proximal-distal plane on the posterior, medial side of the brace 10.

Each of the force straps 18, 20 may include a cushion feature 36 that may be located near or at locations anterior or posterior of the intersection point 21. Moreover, the force straps 18, 20 preferably each have a length adjustment feature 29, such as a hook and loop fastener system, to enable adjustment of the length of such straps 18, 20.

In this embodiment, the force straps 18, 20 are substantially inelastic in order to apply a greater amount of pressure against the knee as opposed to what may occur if elastic straps are used. It has been found that force straps having substantially elastic properties do not effectively unload a knee. Instead, elastic force straps pull the knee into flexion such that when the leg is straightened, the force straps resist flexure of the knee. As a result, while tightening the force straps may indeed unload the knee, the knee is unable to undergo full extension due to the tendency of the knee to go into flexion. Unlike the elastic straps, substantially inelastic straps do not possess these drawbacks since they draw the knee towards a hinge and unload the knee while permitting both flexure and extension of the knee.

It should be understood, however, that embodiments of the knee brace are not limited to usage of substantially inelastic straps. To the contrary, straps of various degrees of elasticity may be employed with the various components in different the embodiments of the knee braces to suit various needs of an individual wearing the brace.

The first force strap 18 is secured to a lateral-proximal bracket assembly 26 and spirals along the posterior of the brace 10 towards the medial-distal side of the sleeve 12. The first force strap 18 then enters in the sleeve 12 and secures to a distal tightening device 23 generally located on the anterior-lateral, distal side of the sleeve 12.

The second force strap 20 is secured to a lateral-distal bracket assembly 27 and spirals around the posterior of the brace 10 towards the medial proximal side of the sleeve. The strap 20 then enters the sleeve 12 and secures to a proximal tightening device 22 generally located on the anterior-lateral proximal side of the sleeve 10. As will be described in the ensuing discussion, the proximal and distal tightening assemblies 22, 23 are provided to incrementally tension the first and second force straps 18, 20, and selectively allow release of tension in the force straps 18, 20.

A proximal stability strap 28 is secured to the medial side of the brace 10 and extends to the lateral side whereat it is connected to a proximal buckle assembly 32 that is connected to the sleeve 12. A distal stability strap 30 is secured to the medial side of the sleeve 12 and extends to the lateral side whereat it is connected to a distal buckle assembly 33 which is also connected to the sleeve 12.

According to this embodiment, each of the stability straps 28, 30 includes a cushion feature 34, such as foam or a textile pad that is secured thereon for enhanced rotational prevention and additional comfort. The stability straps 28, 30 each have an adjustment feature 35, such as a hook and loop fastener system, to enable adjustment of the length of such straps 28, 30. Moreover, the cushion feature may include a frictional feature (not shown), such as a pattern of deposited silicone, rubber, or a mildly abrasive material. In addition, the cushion feature may be breathable, and have a construction similar to the spacer elements described below.

In one variation, the stability straps may be releasably secured to the knee brace. For example, the stability straps may include a snap fastener element that corresponds to a snap fastener element supported by shells of the knee brace. In another variation, other suitable releasable fasteners may be used to permit installation and removal of the stability straps from the knee brace.

An embodiment of the knee brace may be provided alternatively with one force strap connected to a tightening device and another strap that is adjustable with a fastener system such as hook and loop fasteners. For example, in the event that it is desired to provide a low profile brace, one could use a force strap system that is connected to and adjustable at the proximal portion (corresponding to the femur of the wearer) of the brace that includes a tightening device, whereas the force strap system connected to the distal portion (corresponding to the tibia of the wearer) may simply use a hook and loop fastener system. Variations of this embodiment are also useful in order to mitigate issues of a tightening device extending over pressure points that may be present over the tibia.

The embodiment of the brace of FIGS. 7-10 is generally oriented to relieve lateral compartmental osteoarthritis of a left knee. This brace may be configured to treat medial compartmental osteoarthritis of the left leg or, in the alternative, medial or lateral compartmental osteoarthritis of a right knee. The reconfiguration for treating medial compartmental osteoarthritis comprises arranging the force straps in a reverse configuration so the force straps have an intersection point on the proximal-distal plane on the posterior-medial side of the device.

Figure 11:
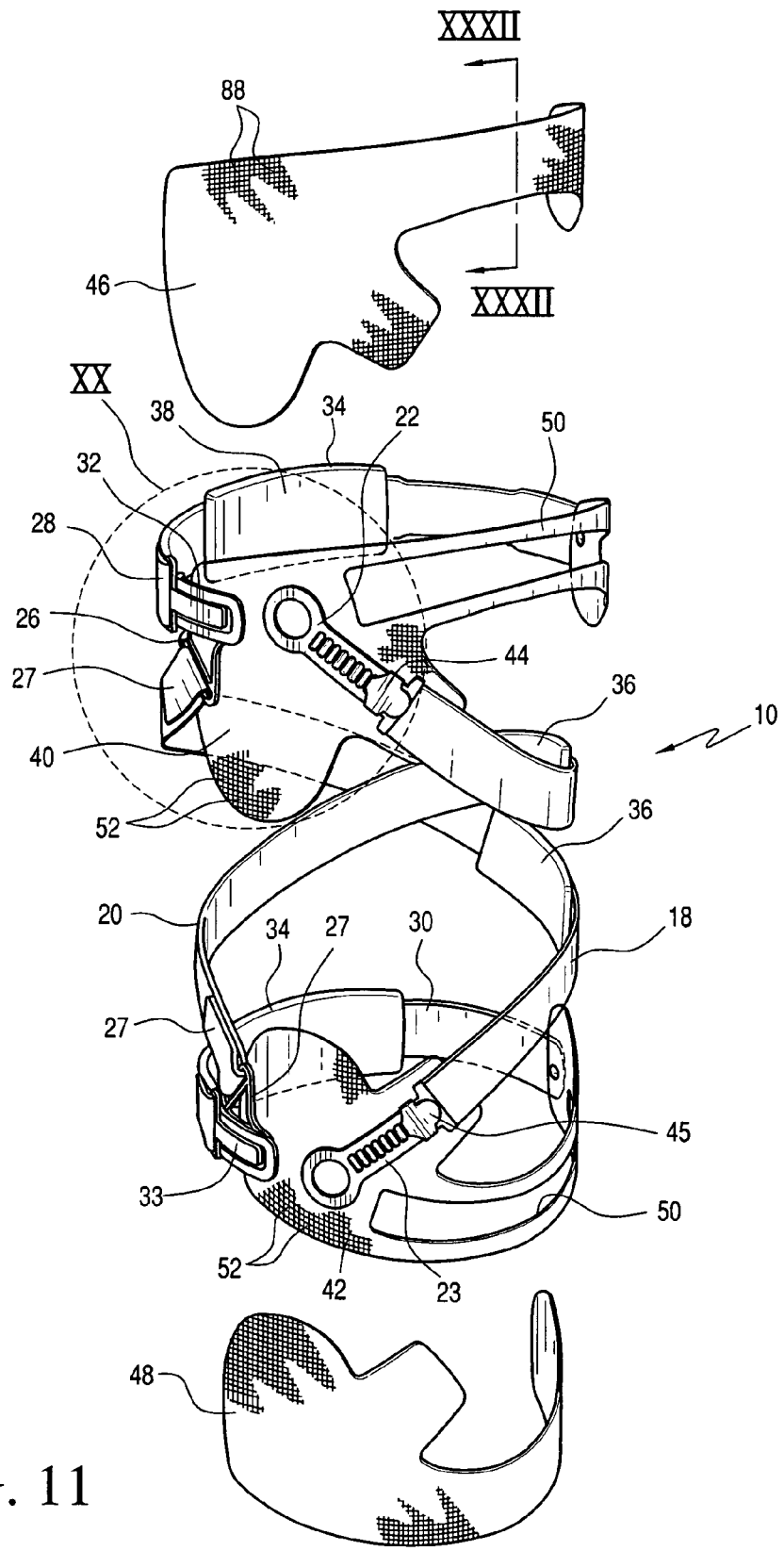
FIG. 11 is an exploded view of the embodiment of FIG. 7 without a sleeve.

Turning to FIG. 11, the internal features of the embodiment of the brace 10 are shown in greater detail without the sleeve 12. Of interest are the proximal and distal shells 40, 42 which provide the structure for brace, and connect to the force straps 18, 20 and the stability straps 28, 30. Of additional interest are the proximal and distal spacer elements 46, 48 which provide anti-rotational means, such as a frictional feature, and cushioning for the brace 10 when worn on a leg.

The proximal and distal shells 40, 42 are configured for placement between the lateral and medial sides of an anterior portion of the brace 10. Similarly, the proximal and distal spacer elements 46, 48 are configured with a shape generally corresponding to the proximal and distal shells 40, 42, and are arranged for connection to a rear portion of the sleeve 12 in register with the shells 40, 42. It is desirable that the proximal and distal shells 40, 42 be in register with the proximal and distal spacer elements 46, 48 so that as the force straps and stability straps are tensioned about a leg. The spacer elements 46, 48 are urged against a leg so as to prevent rotation of the brace 10 due to the forces applied to the leg from the force straps.

According to variations of the shells, they may be configured for placement on the posterior side of the brace, or at least have sections that extend over a portion of the posterior section of the brace. In addition, variations of the shells may involve one shell such as the proximal shell extending about the anterior side of the brace between the lateral and medial sections, whereas the distal shell extends over the posterior side of the brace and further includes a segment wrapping over at least one of the lateral and medial sides to cover a portion of the distal-anterior section of the brace.

A benefit of the spacer elements in a hinge-less knee brace is that these spacer elements prevent migration of the shells towards one another. The spacer elements also maintain the knee brace on the user's leg due to anti-rotation means. Moreover, the spacer elements can also resist any rotational forces that may be applied by the force straps.

ii. Method of Applying the Knee Brace

In operation, the embodiment of the brace according to FIGS. 7-11 is attached to the user, for whom it may be custom made or pre-fabricated, by positioning the device on the leg with the center portion of the sleeve placed over the anterior knee. The proximal and distal force straps 18, 20 are positioned above and below a side of the knee, and tightened accordingly. This arrangement of the force straps ensures that the force straps tighten above and below the knee as the leg moves into extension and loosens as the leg moves into flexion. The tightening of the force straps 18, 20 during extension of the knee prevents movement of the bone upon extension of the leg, and thus treats the adverse affect of compartmental osteoarthritis.

Figure 13:
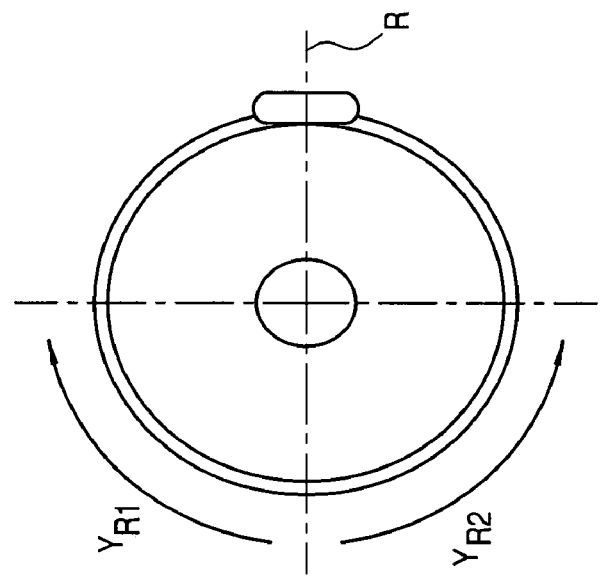
FIG. 13 illustrates the rotational force applied on a leg by the brace of FIG. 7.
Figure 12:
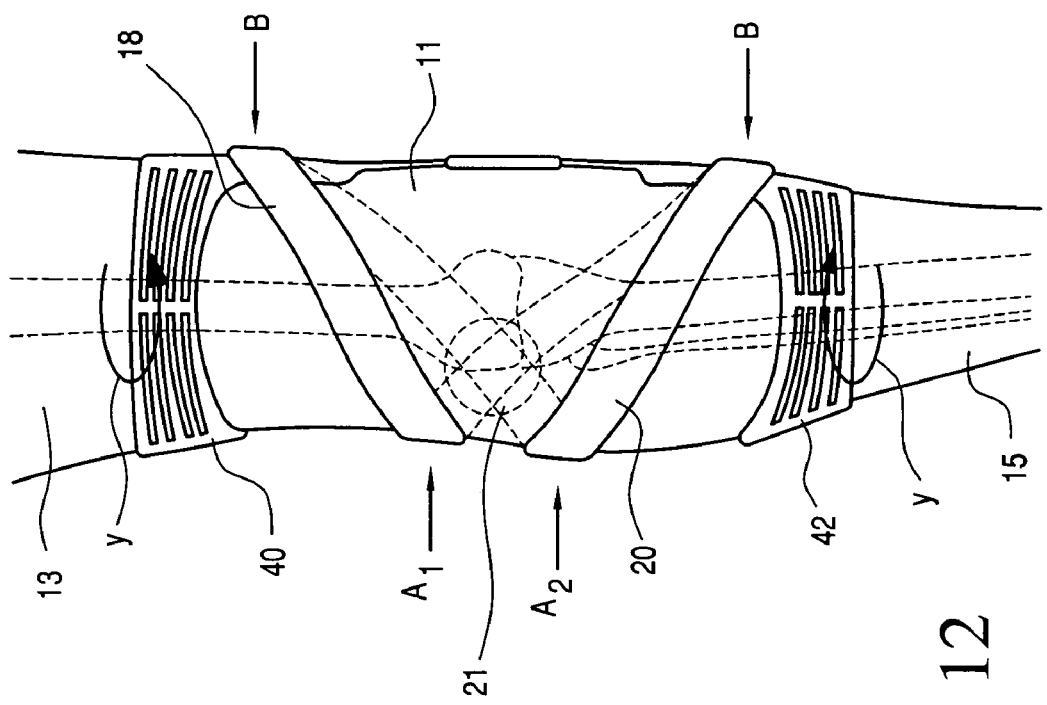
FIG. 12 is a schematic view of forces applied on a leg using the brace shown in FIG. 7.

FIGS. 12 and 13 illustrate the brace on a left leg 11 that defines proximal and distal portions corresponding to the femur and tibia, respectively. The tightening of the force straps 18, 20 tend to depressurize the compartment of the knee by increasing the space between the bones on the affected side of the knee. The configuration of the force straps along the frame elements 40, 42 provides reaction points for the force straps 18, 20. Thus, tightening of the force straps 18, 20 causes the frame elements 40, 42 in combination with the spacer elements to stabilize the knee on the side opposite the intersection area 21.

Figure 1:
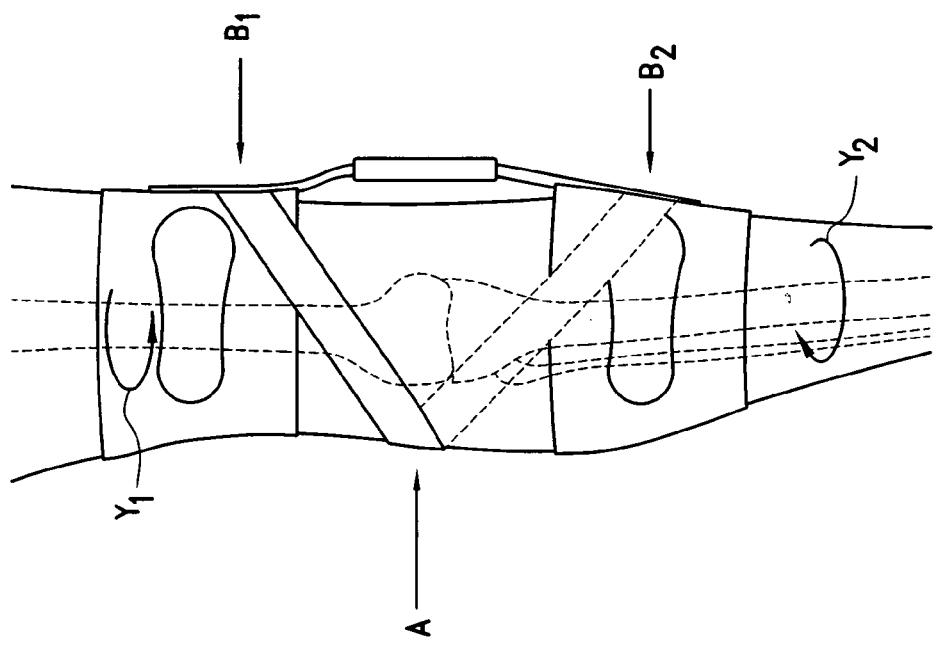
FIG. 1 is a schematic view of forces applied on a leg using a prior art knee brace.

From FIG. 12, the forces $A_1$ and $A_2$ are shown applied to the medial side of the knee at a greater degree than the single force A generated by the prior art braces, as exemplified in FIGS. 1 and 2, due to the greater distribution of pressure on the leg. Additional forces B are applied on the lateral side of the leg approximately where the force straps are attached to the proximal and distal members. By applying two forces, these forces counteract to mitigate the rotational moment that is present in the prior art braces wherein rotational forces $Y_{R1}$ and $Y_{R2}$ are generally equal to and cancel one another.

It has been found that if only one force strap is used without any intersecting points, as in the prior art braces, the skin and soft muscle tissue move with the shells. As a result, the unloading effect of the straps decreases significantly. By using the two force straps to form forces $A_1$ and $A_2$, rotation of the device on the leg is reduced and effectively prevented. This provides a sufficient unloading effect by the brace on the knee.

The force straps are substantially inelastic since, as mentioned previously, it has been found that in prior art braces that employ elastic force straps, the knee and leg counteract the suppleness of the elastic straps thereby reducing the unloading effect on the knee. By using substantially inelastic force straps, the knee is unable to resist the straps and, consequently, a greater unloading effect is obtained of the knee.

Figure 15:
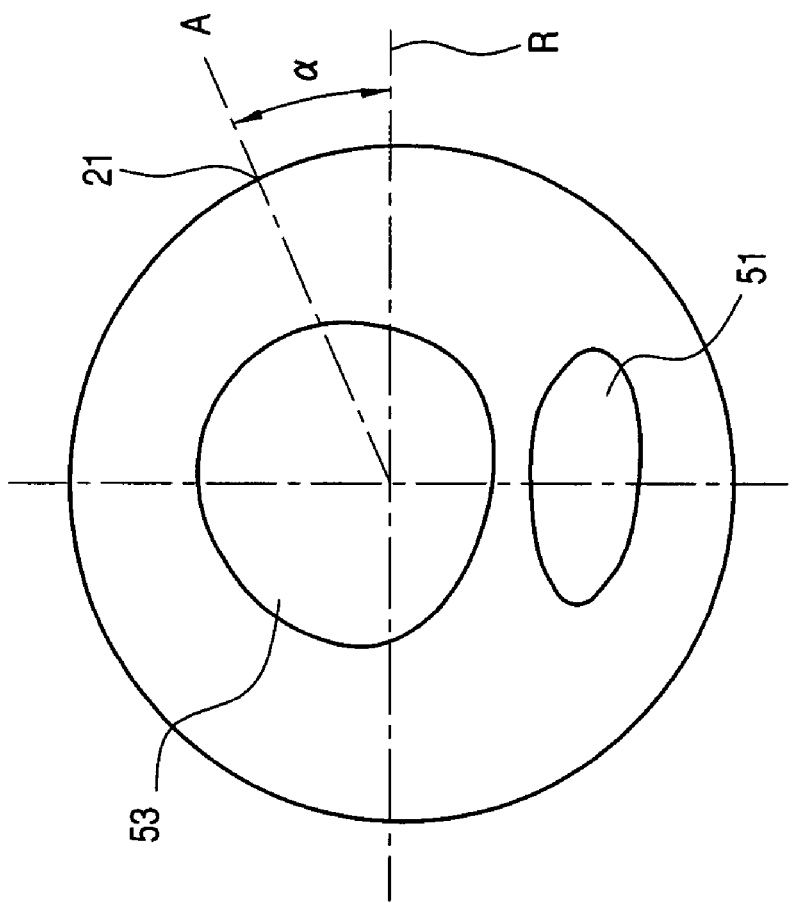
FIG. 15 is a sectional view taken along line XV-XV of FIG. 14.
Figure 14:
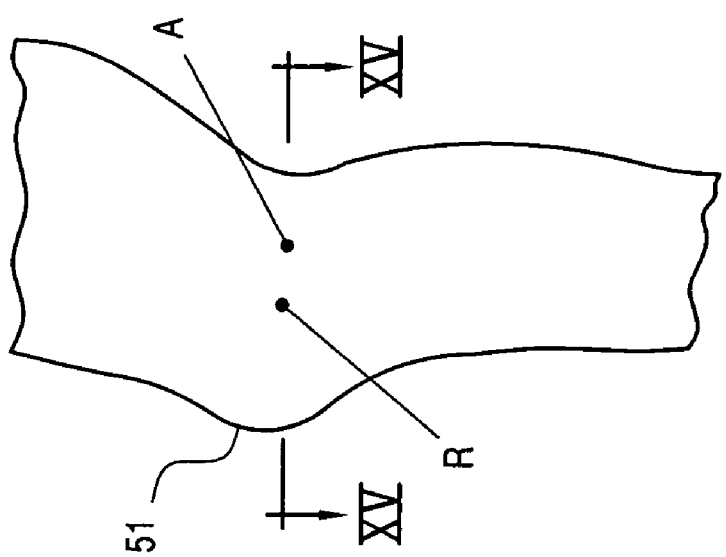
FIG. 14 generally illustrates where the force is applied externally of the knee in the brace of FIG. 7.

Referring to FIGS. 14 and 15, the resultant force "A" of forces $A_1$ and $A_2$ in FIG. 12 is applied as the knee goes into extension. The force straps preferably cross at intersection point 21 at angle α ranging about 5° to 20° posterior of the normal axis of rotation of the knee with the knee cap 51 being in front of rotational axis R and tibia 53. The intersection point is preferably not the point of unloading; instead, the unloading point is directly on the lateral side for the medial brace, and directly on the medial side for the lateral brace.

The knee brace may be tailored to optimize the forces generated by the force straps. When the brace includes two force straps or has a single force strap with two intersecting portions, a greater moment is applied to a leg providing that the same force is now applied by two force straps. This results in a lower angle that may be used to configure the force strap(s), and consequently proximal and distal frame members or shells may be positioned closer together as opposed to in prior art braces having only a single force strap which spirally extends once between proximal and distal members.

In following discussion, descriptions and variations of the specific components pertaining to the inventive knee brace are described.

iii. Straps

The force straps and stability straps may be constructed from a variety of different textiles and other suitable materials. According to one variation exemplified in FIGS. 16 and 17, the force strap 400 and stability strap 412 are shown as comprising a two layer system; an inner core 404, 416 surrounded by an outer layer 402, 414. Suitable stitching 406, 420 is provided to secure the inner core 404, 416 and outer layer 402, 414 together. When viewed from a rear end, the two layer system combines to form a C-folded strap wherein the outer layer 402, 414 wraps around the inner core 404, 416 to generally define an elongated C-shape about the corners of the strap.

The inner core 404, 416 is preferably constructed from a soft loop material. This material is generally soft to the touch so that for a knee brace having the strap extend about the popliteal (back of the knee); the worn strap is comfortable to the wearer of the brace. This is evidenced when the wearer flexes his leg as well as when the leg is fully extended. The compliance and softness of the inner core mitigates the need for a cushion feature of the very type shown in FIGS. 7-10.

The outer layer 402, 414 may be constructed from any suitable textile since the compliance of the strap is essentially provided by the inner core 404, 416. This enables the use of a cosmetically pleasing or a substantially inelastic material.

Both of the straps 400, 412 may include a tab 410, 418 located at the front end of the straps to provide adequate reinforcement to this area. The tab 410, 418 may comprise a plastic or metal piece that is secured to the front end of the straps by a press fit, stitching, adhesive or other suitable means. In addition, as will be discussed in further detail below, the force strap 400 may include indicia 408 representative of incremental settings of the strap.

In yet another variation, the stability straps may be substantially stretchable and secured to the sleeve or shells. The straps according to this variation may be configured so that they are dimensioned so as to permit the brace to be donned and doffed by being slidable on a leg of an individual wearing the brace, but sufficiently tensioned so as to wear tightly on the individual's leg.

iv. Shells

Figure 7:
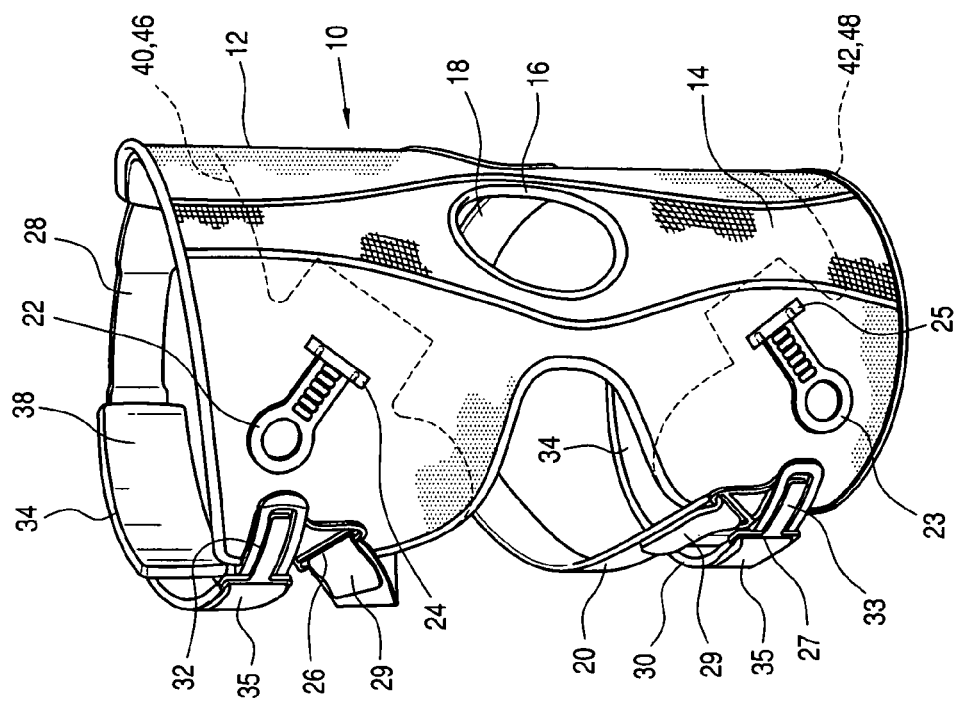
FIG. 7 is a perspective view of an embodiment of a knee brace of the invention.
Figure 10:
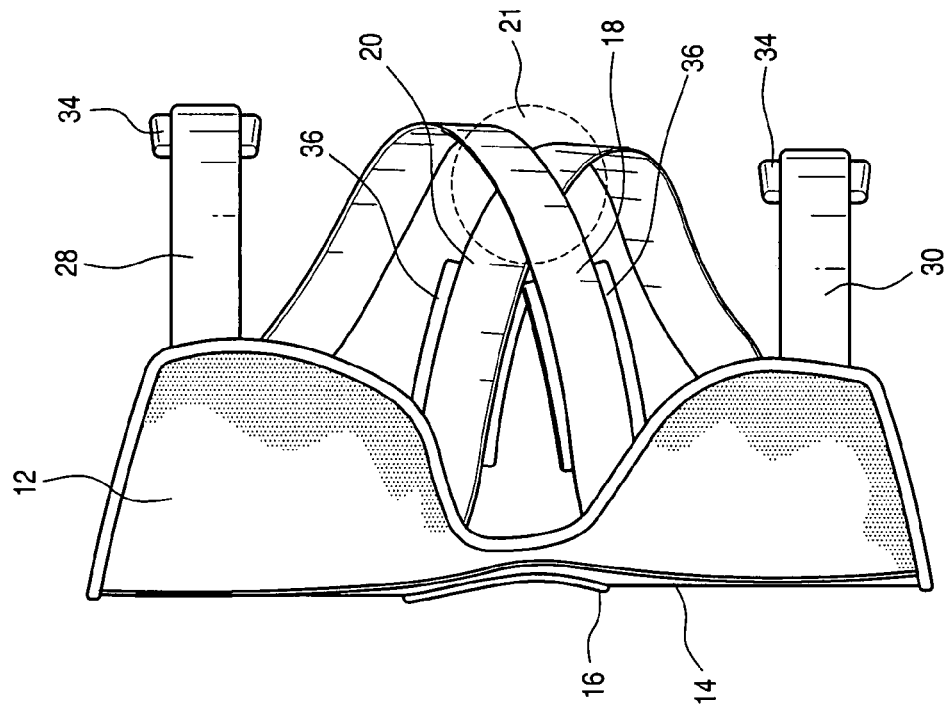
FIG. 10 is a lateral side elevation view of the embodiment of FIG. 7.
Figure 9:
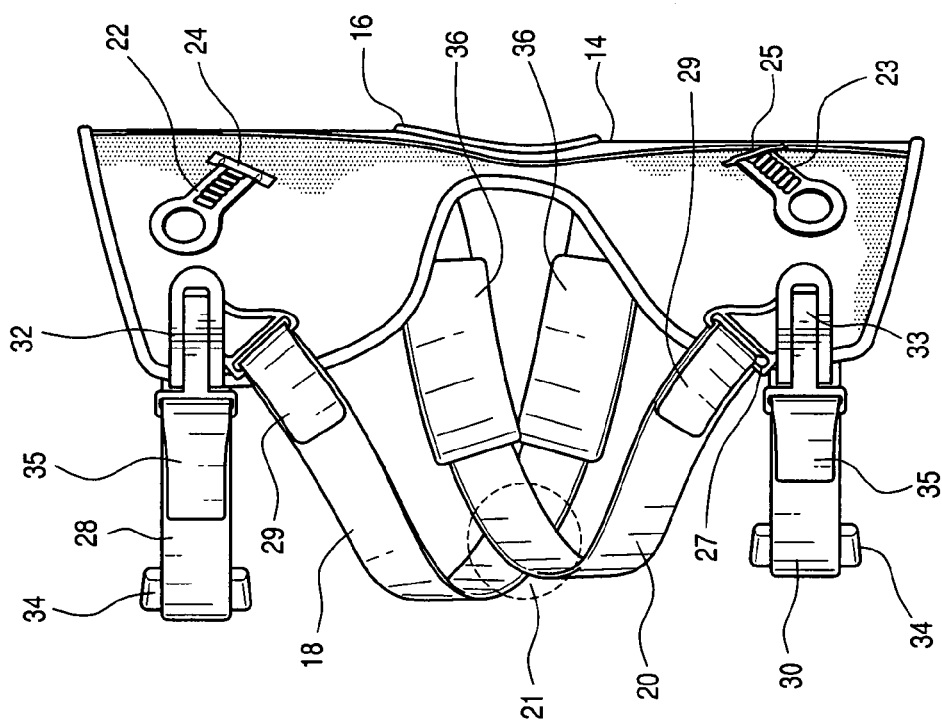
FIG. 9 is a medial side elevation view of the embodiment of FIG. 7.

FIGS. 18 and 19 illustrate one variation of the proximal and distal shells 40, 42 of the brace of FIG. 7. Each of these shells 40, 42 has a perforated structure 52 which ventilates the brace and therefore mitigates heat build-up when the brace 10 is worn on a leg. Moreover, each shell has a clearance 50 which extends between the lateral and medial sides thereof as a further ventilation feature. While the shells 40, 42 are of sufficient rigidity and strength to withstand forces exerted by the force straps 18, 20 and the stability straps 28, 30, the shells 40, 42 may be flexible to conform to corresponding portions of a leg.

Because the shells 40, 42 have a perforated structure 52 and a clearance 50, the shells may be sized larger than other known structural features or frame members known in the knee bracing art. For example, the proximal shell 40 has an enlarged first side portion 54 that provides sufficient support against a leg and can accommodate the tightening device 22 and buckle assembly 26. The shell 40 also defines a protruding section 56 extending from the first side portion 54 in a direction generally tracing the path of the second force strap 20 so as to distribute the pressure of the strap against the leg.

The shell 40 defines a second portion 58 that is sufficiently large to secure to a leg, yet is of minimal size to prevent excessive intrusion on a corresponding side of a leg. Similarly, the distal shell 42 defines features corresponding to the proximal shell 40, such as an enlarged first side portion 68, a protruding section 70, and a second side portion 72.

As exemplified in FIGS. 20 and 21, each of the shells 40, 42 preferably has provisions for mounting the tightening devices 22, 23, the bracket assemblies 26, 27, and the buckle assemblies 32, 33. The shells 40, 42 may each include an opening 66 for receiving a mounting feature 82 of a tightening assembly, and an eyelet 62 located on the lateral portions 54, 68 which is arranged to receive corresponding pins or similar features 82 of the bracket assemblies 26, 27 and buckle assemblies 32, 33. The eyelet 62 defines a seat portion 64 in which the mounting feature 82 of the bracket and buckle assemblies, such as a pin, button, flange, hook, or similar element, are urged and retained there against. The seat portion 64 is defined as a reduced portion of the eyelet 62 having a radius just larger than the mounting feature. Also, FIG. 19 shows a similar construction with eyelet 63 and seat portion 65 on the shell 42.

The construction of the eyelet of this embodiment is particularly advantageous in that it facilitates detachment of the buckle assemblies and bracket assemblies from the device when not worn on a leg. For example, when the force straps and stability straps are de-tensioned, or the brace 10 is not worn, the mounting feature 82 may be urged from the seat 64, and subsequently removed from the shells 40, 42. However, when the straps are in tension, the mounting feature is urged and locked in register with the eyelet seat 64.

In a variation of this embodiment, individual eyelets of the type described above may be defined on the shells for individually accommodating both a buckle assembly, and a bracket element having a mounting feature. According to another variation of this embodiment, either of the buckle assembly or bracket element may have a hook which is securable against a corresponding eyelet defined in the shells. In yet another variation of this embodiment, the bracket element and buckle assembly may be permanently secured onto the shells using means such as rivets or other known fasteners.

Figure 22:
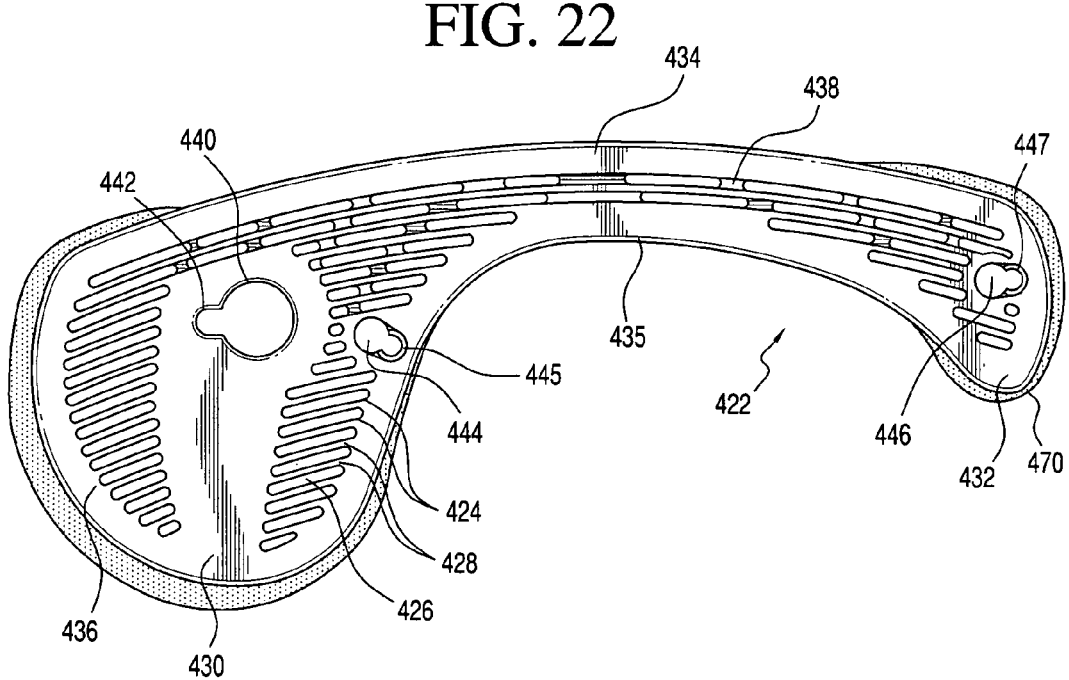
FIG. 22 is a front elevational view of another variation of a proximal shell.
Figure 23:
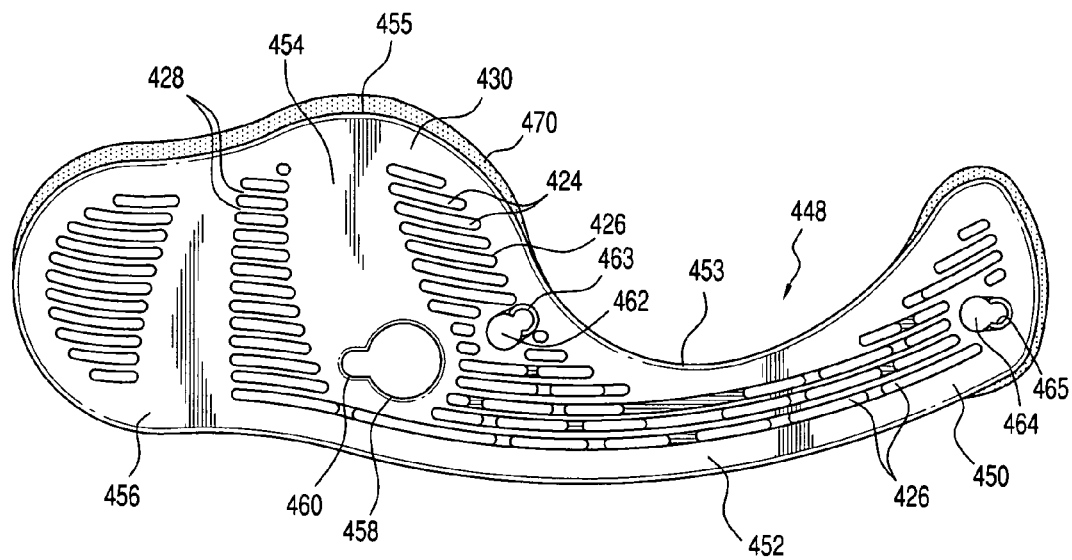
FIG. 23 is a front elevational view of another variation of a distal shell.

In accordance with another variation of the shells, FIGS. 22 and 23 show proximal and distal shells 422, 448 having a different perforated structure 424 from the embodiments of FIGS. 18 and 19. Specifically, the perforated structure 424 comprises a plurality of generally horizontal slots 426 extending along segments across the width direction of the shells 422, 448. These slots 426 are interspersed with a plurality of slats 428 or are generally laterally spaced by material segments 438. Frame portions 430 of each of the shells 422, 448 surround the slots 426 and slats 428.

The shape of the proximal shell 422 generally resembles the shape of the proximal shell shown in FIG. 18. Particularly, the proximal shell 422 defines a second side portion 432 that extends downwardly from a transverse portion 434 corresponding to the anterior-proximal portion of the shell and spanning to a first side portion 436. The transverse portion 434 includes an arcuate profile that is preferably pronounced on the distal side thereof and conforms to the anatomy of a thigh. The first side portion 436 extends downwardly beyond the distance extended by the second side portion 432, and is generally wider in size than the second side portion 432 to provide additional support on the leg.

The proximal shell 422 includes an eyelet 440 located on the second side portion 430. The eyelet 440 is configured for receiving a pin or locking device of a buckle assembly. A seat 442 is located on a side of the eyelet that is preferably distant from the second side portion 432 of the shell. The seat 442 may form a slot extending from the eyelet 440 and has a smaller diameter than the eyelet 440.

The proximal shell 422 also includes a slot 444 that is separate and larger than the slots 426, and is located near the transition between the first side portion 436 and the transverse portion 434. Preferably, the slot 444 is directed at an angle relative to the slots 426. The slot 444 includes a compliant edge 445 that is located at a side thereof closest to the transverse portion 435. The complaint edge 445 imparts a smaller effective height for the slot 444 and is arranged for receiving a pin, knob or other securing means carried by the ratchet assembly, as described more fully connection with FIG. 43.

The compliant edge 445 is formed of a material that is preferably more flexible than the material used to form the proximal and distal shells, 422, 448. For the example, the compliant edge 445 may be a silicone rubber or a suitable polymeric material.

The proximal shell 422 also includes a slot 446 that is located at the second side portion 432 of the shell. Similarly, the slot 446 is located at an angle relative to the slots 426 and likewise includes a compliant edge 447 that is located at an end portion remote from the transverse portion 434.

The shape of the distal shell 448 differs from the shape of the distal shell 42 shown in FIG. 19. Specifically, the distal shell 448 includes a second side portion 450 that connects to a transverse portion 452 corresponding to the anterior-proximal portion of the shell. The transverse portion 452 has a proximal arcuate profile 453 that is generally contoured to the shape of a shin of a human leg. From the transverse portion 452, a proximal side of the distal shell rises to apex 455 which provides additional support to the wearer at a first side portion 454 of the shell 448. The shell 448 also includes a calf extension member 456 that protrudes from the second side portion 454 of the shell 448.

The calf extension member 456 extends to the posterior section of the brace when worn on a leg. The calf extension member 456 has the benefit of preventing the shell 448 from rotating when the knee brace is worn on a leg, and also serves as an additional suspension feature since it is preferably configured to extend over the thickest point of a human calf. Another benefit of the calf extension member 456 is that it removes the necessity of two stability straps for connection to the distal shell since the calf extension member effectively provides substantial support about the calf.

The distal shell 448 includes an eyelet 458 that has a seat portion 460 which is similarly constructed as the eyelet 440 and seat portion 442 of FIG. 20. The distal shell also includes a slot 462 and a corresponding compliant edge 463 that generally corresponds to the same location with the exception of their orientation as the slot 444 and respective rim 445 in FIG. 20. Also, the distal shell has a slot 464 and a respective compliant edge 465 that corresponds in location with the exception of orientation to the slot 446 and respective rim 447 in FIG. 20.

The shells 422 and 448 may include a compliant feature 470 disposed about the entirety or at least portions about their periphery. The compliant feature is constructed of a material that is more flexible than the material comprising the shell bodies. The compliant feature 470 extends beyond the outer perimeter of the shells. The compliant feature is preferably a flexible resilient material that is secured to the shells by bonding, mechanical interlocking or any other suitable arrangement. An example of a method for providing the compliant feature is described in U.S. Pat. No. 5,445,602, incorporated herein by reference.

The shells may be custom sized and contoured to accommodate the leg of a wearer of the brace. Also, the shells may be preformed to curve to the contour of a leg, or curved as a result of the straps and sleeves causing the shells to curve about the leg of a wearer of the brace. While the embodiments described herein assume the shells to be sufficiently flexible to accommodate a wearer's leg in both extension and flexion of the knee, the shells can also be configured to be substantially rigid as in prior art braces.

The proximal and distal shells of these variations may be constructed of variety of materials such as TRIAX (abs/nylon blend), polypropylene, polyethylene, nylon, carbon or glass fiber prepeg with thermosetting or thermoplastic resins, and rigid foam from EVA, platezote or polyurethane. In another variation, the proximal and distal shells may be constructed similarly to the orthotic sleeve described in U.S. Pat. No. 6,592,539 assigned to Ossur hf of Reykjavik, Iceland, and incorporated herein by reference.

The perforated structure of the shells enables the shells to be sized larger than most frame members used in knee braces. As a result, the pressure exerted against the leg by the force straps can be more evenly distributed about the leg.

Figure 24:
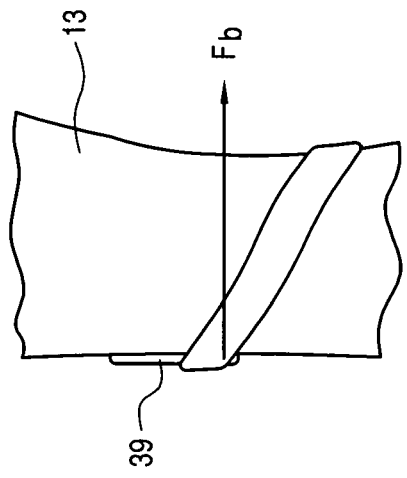
FIGS. 24-27 are force diagrams showing pressure distribution across prior art frame members and the proximal shell of the brace in FIG. 7.
Figure 25:
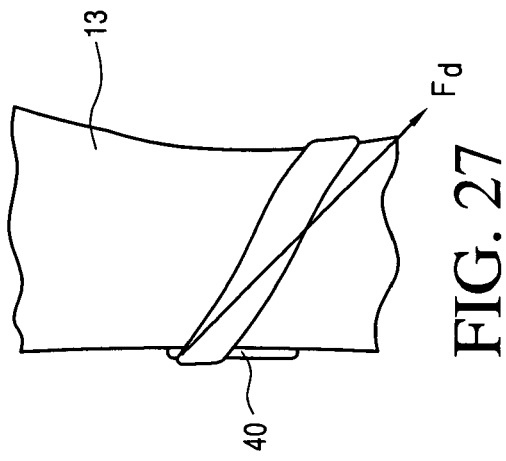

FIGS. 24-27 schematically show how the shells of the aforementioned embodiment of the knee brace are advantageous over those in known knee braces. FIG. 24 schematically shows a hypothetical horizontal force $F_a$, corresponding to the direction of a force strap, extending from a midpoint of a prior art shell 39. In this arrangement, pressure from the force $F_a$ is evenly distributed across the shell 39 and across leg 13. FIG. 25 shows hypothetical horizontal force $F_b$ extending from a distal portion of shell 39. In this arrangement, the force $F_b$ exerts greater pressure across the leg 13 at the bottom of the shell than at the top of the shell.

Figure 26:
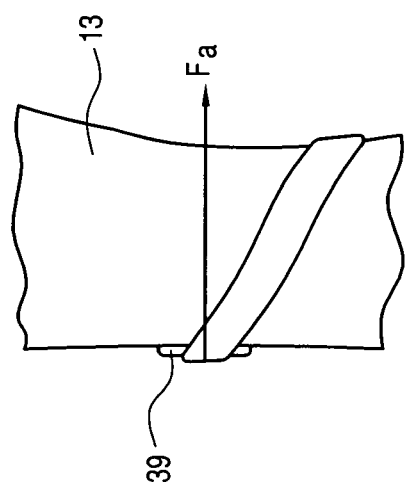
Figure 27:
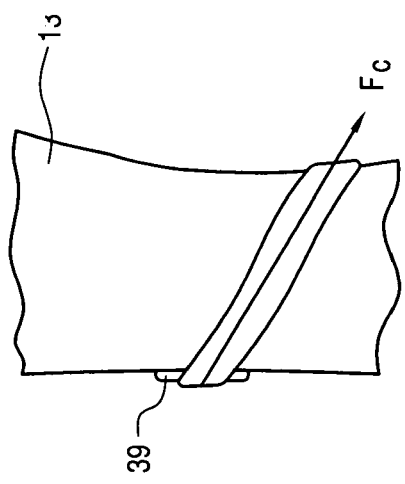

FIGS. 26 and 27 more aptly exemplify the actual force exerted by a force strap on a proximal shell. FIG. 26 shows a shell 39 in the prior art having a small size in order to minimize weight of the brace and the generation of heat due to the shell being worn against a leg. Because the shell is small, the force strap is secured to a center portion of the shell and diagonal force $F_c$ creates greater pressure on a lower portion of the shell across the leg 13 than at the upper portion.

FIG. 27 shows shell 40, wherein due to the ability to provide a larger shell, the force strap can be mounted at the upper portion of the shell. This results in diagonal force $F_d$ which corresponds to a greater portion of the shell than the force $F_e$, and thereby more evenly distributes pressure from the force $F_d$ over the shell and across the leg 13. By placing the force strap above the middle portion of the shell, one can obtain better distribution of pressure over the shell.

It has been found with known prior art knee braces that when force straps are not located at the same positions at both proximal and distal frame members, rotation of the frame members may occur. Since these frame members have a tendency to be significantly smaller than the shells according to the aforementioned knee brace embodiment, they are often located closer together, and proximate to the knee.

Particular benefits of the shells of the aforementioned embodiment are discussed in the following examples. In these examples, it is assumed that a force strap is provided which is pulled with a 10 N force, and the width of the knee or distance x is the same. In the first instance, the distance Y, which is defined as the distance between the shells, is 6 units. By moving the distance Y to 8 units, a greater moment due to the leverage arm is formed by the distance of the shells. Because of the increase in distance Y, the vertical force caused by the force strap is increased as a result of the change in angle of the force strap. Consequently, the shells are more strongly urged towards one another. On the other hand, the horizontal force is reduced so that the pressure on the knee in the horizontal direction is reduced, even though there is a greater moment applied to the knee.

It follows that if the shells are moved closer together, for example back to 6 units in distance, the moment is reduced yet there is more horizontal pressure on the knee. Moreover, the force exerted by the force strap must be increased in order to achieve the same amount of moment as created when the shells are separated by 8 units which results in yet more horizontal force about the knee. By providing the dual force strap arrangement, it is readily evident that the dual force strap provides two points of pressure and two straps creating a load on the knee. Therefore, the knee brace is more comfortable when unloading a knee since there is greater pressure distribution.

In addition to the advantages of the shells regarding pressure distribution, the shells can be arranged to extend over a greater portion of the leg than in known frame members. For example, prior art braces have small frame members that extend minimally about the leg, and the frame members have a tendency to rotate about the knee when the force straps are unloading the knee. This results in minimal tibia hyperextension and ligament control.

v. Sleeve

Figure 28:
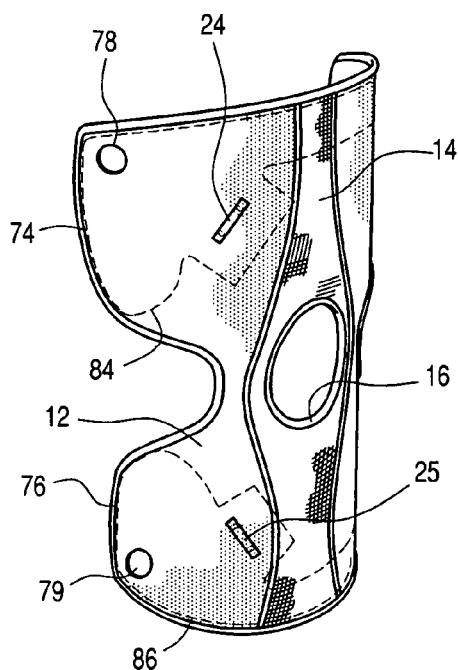
FIG. 28 is a frontal perspective view of the sleeve of FIG. 7.
Figure 29:
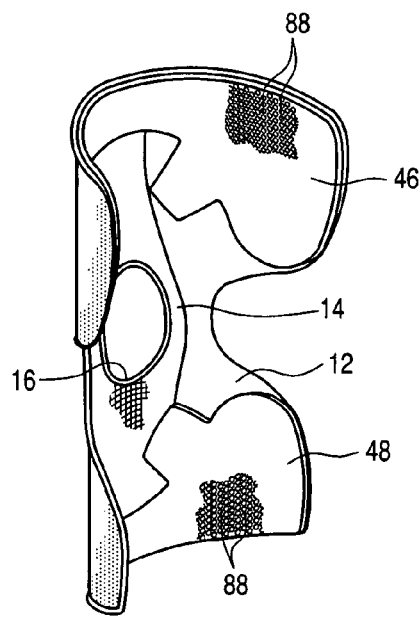
FIG. 29 is a rear perspective view of the sleeve of FIG. 7.

FIGS. 28 and 29 illustrate an embodiment of a sleeve 12 and the spacer elements 46, 48 that form proximal and distal pockets 84, 86 therebetween. The pockets 84, 86 include proximal and distal openings 74, 76. The openings 74, 76 may be closeable with closing means such as hook and loop fasteners, zippers, buttons, and other suitable means. The openings 74, 76 are configured for permitting insertion of the shells 40, 42 into the pockets 84, 86 which are shaped to closely conform to the shape of the respective shells 40, 42. The sleeve 12 further defines proximal and distal eyelets 78, 79, which correspond to the proximal and distal eyelets 62, 63 of the shells 40, 42.

In a variation of the embodiment of FIGS. 28 and 29, the sleeve includes pockets within the sleeve itself, wherein the shells are insertable into the pockets, and the pockets are closeable with a suitable fastener feature, such as with hook and loop fasteners, stitching, rivets, and other known means readily available to a skilled artisan. The spacer elements are secured against a rear portion of the sleeve corresponding in shape and location to the shells.

In another variation, the sleeve and spacer elements may be secured to one another so that the pockets form at the lower side of the proximal section and the upper side of the distal section. According to this variation, the shells may be inserted into the pockets so that the spacer elements and sleeve effectively cover the shells, yet so that the shells are easily removed from the sleeve and spacer elements. This also enables the shells to slide into the pockets while the shells are still connected to one another.

In yet another variation, the shells may be secured, either permanently or removable, to the posterior side of the sleeve with a suitable fastener feature. In yet another variation, the brace may be provided without the sleeve, and simply possess the structure shown in FIG. 11, wherein the spacer elements are secured to the shells by a suitable fastener feature. A hinge may be used to connect the shells, or other suitable connecting elements may be used to prevent the shells from being drawn towards one another when the brace is provided without the sleeve.

In yet another variation of the sleeve, the sleeve comprises proximal and distal portions that are separate from one another. According to this variation, the proximal and distal portions may include the aforementioned pockets for retaining the shells, or in the alternative, the shells may be secured to a surface of the sleeve portions. According to this variation, the sleeve portions may be connected by a hinge located on one of the lateral or medial side of the brace, or with one of the other connecting element described herein.

Figure 30:
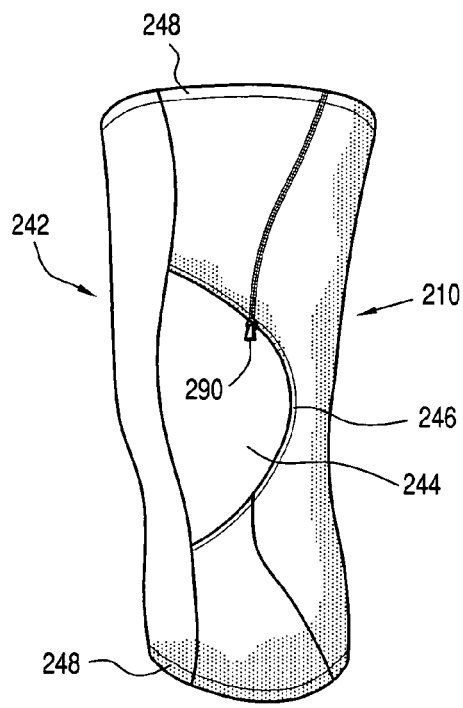
FIG. 30 is a front elevational view of a sleeve embodiment for the knee brace.

Another variation of the sleeve is shown in FIG. 30 wherein the sleeve 242 is configured for enveloping frame elements and is removable therefrom. According to this variation, the sleeve 242 generally conforms to the outer surfaces of the proximal and distal members, and preferably envelopes the outer surfaces of the aforementioned features of the knee brace. The sleeve 242 includes an opening 246 that generally corresponds to an anterior knee. This provides access to the knee cap and is located at a portion of the sleeve that is subjected to bending of the knee.

Encircling the opening 244 is a first beveled portion 246 that eases the flexion of the sleeve 242 during gait. In addition, the sleeve 242 is provided with a second beveled portion 248 disposed along the proximal and distal edges. The first and second beveled portions 246, 248 relieve the brace of any sharp or blunted edges that may catch on clothing, and are thus provided to facilitate the donning of clothing over brace.

The sleeve 242 may be applied over the underlying features of the knee brace in a variety of manners. According to the variant shown herein, the sleeve 242 takes the form of a socket that surrounds the underlying features. Also, the sleeve 242 may include pockets wherein proximal and distal shells may be inserted therein, and means on the exterior of the sleeve for securing spacer elements. The sleeve may be unrolled from a rolled up condition for donning over the underlying features, and is secured thereon due to elasticity of the sleeve or, in the alternative, by hook and loop fasteners or other suitable means.

Figure 31:
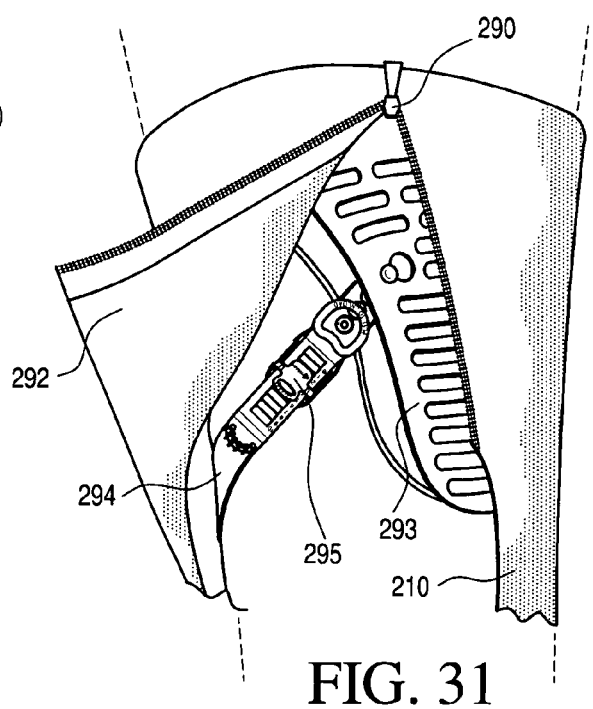
FIG. 31 is a perspective view of a feature of the sleeve of FIG. 30.

The sleeve 242 may include a zipper 290 located along one side of the proximal section thereof. As shown in FIG. 31, the zipper 290 provides an access 292 to a tightening mechanism 295 secured to a proximal shell 293 and a force strap 294. This particular variation allows for concealment of the tightening mechanism 295 under the sleeve 242, yet still permits facile access for adjusting the tightening mechanism. Moreover, this variation prevents the tightening mechanism from catching on clothing or any other objects that the leg may come into contact with, and further provides for a more cosmetically pleasing brace. The proximal portion of the sleeve can have a similar zipper and access to the distal shell.

The sleeve may be constructed of a fabric including spandex, lycra, nylon, polyester, OUTLAST, COOLMAX, AEROSPACER, microfiber, three-dimensional fabrics, and other suitable fabrics. The sleeve may have various treatments incorporated therein such as antibacterial, scenting, and moisture wicking agents.

In yet another variation of the sleeve, the sleeve may be constructed as the orthotic sleeve in U.S. Pat. No. 6,592,539 wherein elasticized fabric is used to form the sleeve and is arranged in different sections that exhibit different elastic stiffness in lengthwise and widthwise directions of the fabric. That is, the fabric is essentially stiffer in one direction than in a direction perpendicular to the one direction.

vi. Spacer Elements

As shown in FIGS. 11 and 29, the brace 10 includes proximal and distal spacer elements 46, 48 that are contoured in a similar configuration as the shells 40, 42. These spacer elements 46, 48 are arranged so as to be breathable by permitting a free flow of air therethrough. The spacer elements also preferably include a friction feature, as in a frictional layer, on at least one side thereof.

The spacer elements may be connected to the sleeve via removable means, such as with a hook and loop fastener system, or may alternatively be secured to the sleeve via stitching, adhesives, or other similar fastener features. While the spacer elements are intended not to interfere with the motion of the knee, they are intended to provide sufficient frictional force and cushioning to maintain the shells against the knee due to the vertical forces created by the force straps.

According to this embodiment, the spacer elements 46, 48 are secured to the posterior side of the sleeve 12. The spacer elements 46, 48 have a breathability feature 88. According to a variation, the breathability feature comprises a pattern of openings defined across the spacer elements 46, 48. Alternatively, the breathability feature may comprise a breathable fabric, and may be combined with a pattern of perforations to further enhance the breathability of the spacer elements. Moreover, the spacer elements may be constructed from a material that provides cushioning and further compresses, at least in part, when the brace is worn.

Figure 32A:
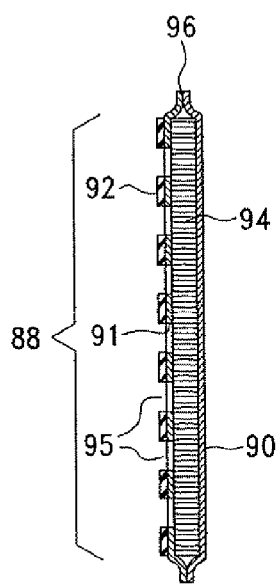
FIG. 32A is a sectional view taken along line XXXII-XXXII of FIG. 11.

According to one variation of the spacer element 47 exemplified in FIG. 32A, which is a cross-section of the spacer element 46 in FIG. 11, the spacer element 47 preferably has a breathability feature defined by an apertured friction feature in the form of a frictional layer 92 that is provided on an apertured first surface 91 of a ventilated and compressible core 94. The frictional layer 92 preferably has a high frictional coefficient against the skin or clothing.

Through the apertured first surface 91 and an opposed second surface 90, the core 94 permits the passage of air therethrough, and yet is compressible to provide adequate cushioning and securing to a leg or other anatomy. In addition, the spacer element has a reinforced edging 96 protecting the core portion, and enhancing the durability of the spacer element. The reinforced edging may comprise a material separate from the core or frictional layer, such as a hook-receivable material, as explained in detail in connection with the variation of FIG. 32C.

Figure 32C:
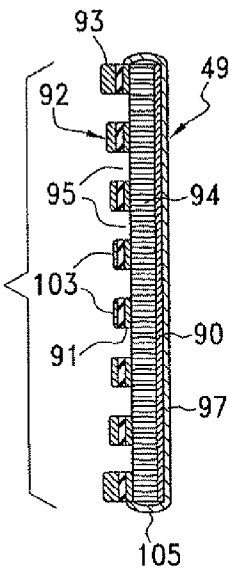
FIG. 32C is a sectional view of another variation of a spacer element.
Figure 32B:
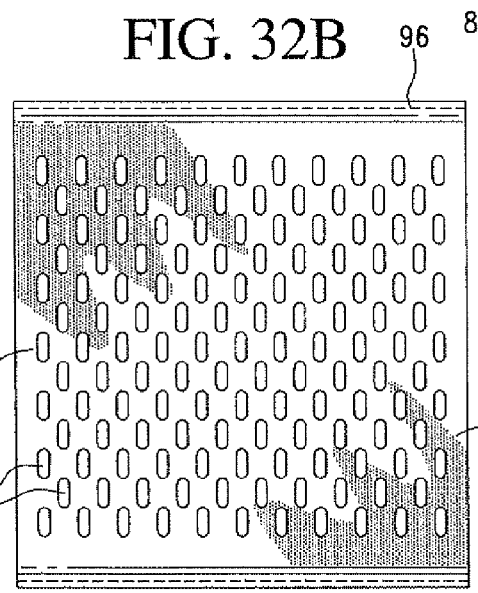
FIG. 32B is a schematic elevational view of the spacer element of FIG. 32A.

In observing FIG. 32B, the breathability feature 88, located on at least on one side of the spacer element 47, is defined by the pattern of apertures 95. Preferably, the apertures 95 of the frictional layer 92 and the apertured first surface 91 coincide with one another so that they are common with one another as exemplified by the apertures 95 in FIG. 32B.

In this variation, the frictional layer 92 is generally discrete resulting in a distinct and separate layer. The frictional layer may be free standing so as to be applicable onto the first surface of the core as an already-cured sheet, or may be deposited or formed onto the first surface of the core so as to be laminated or alternatively coated onto the first surface of the core. The frictional layer may be secured to the core through bonding with an adhesive, lamination under suitable heat and pressure, or coating of the core with uncured or partially cured compositions.

An exemplary method may be adapted from U.S. Pat. No. 7,161,056, owned by the assignee of this disclosure and incorporated herein by reference. According to this method, an uncured silicone composition is molded to a particular configuration in the form of a layer at a suitable curing temperature. After a period of curing, the thus formed partially cured silicone composition layer is applied to or pressed against a substrate, and is continuously cured until curing is complete. By molding the frictional layer at least partially prior to application onto a substrate, one can tailor the shape of any apertures or pattern that the frictional layer may take.

According to this variation, the frictional layer 92 is generally continuous so that it forms a web-like structure. The apertures 95 of the frictional layer 92 may be formed in a predetermined pattern that may or may not be independent from the apertures or any ventilation feature of the core. In alternative variations, the frictional layer may be provided in a pattern of distinct segments and locations, so that it is not continuous as in the web-like structure. Such segments may comprise lines, dots or other individual shapes.

It will be noted, however, that the apertures of the frictional layer and the core, as either with or without the first surface, must not necessarily coincide with one another. For example, the core may be an open-cell foam having a plurality of random pores located along the surface thereof. The frictional layer, on the other hand, may have a pattern of uniformly spaced apertures independently provided from the pores of the foam. What is important is that at least some apertures of the frictional layer and the core intersect so as to permit the transfer of air through the spacer element.

An example of providing a frictional layer over a core such that the apertures of the frictional layer do not correspond to apertures or pores of the core is found in U.S. Pat. No. 7,161,056. It will further be pointed out that the frictional layer of this invention may be applied to non-apertured substrates for particular applications wherein it is not necessary that the substrate be breathable but wherein it is desirable that there is some form of frictional resistance provided on the substrate.

In another variation of a spacer element 49, as shown in FIG. 32C, the second surface 90 of the core 94 is secured to a hook-receivable material 97. This enables the spacer element to be easily secured to corresponding hook material with may be secured to the shell of a brace. Also, by providing hook-receivable material on the spacer element 49, the surface of the spacer element is soft to the touch, and enables the spacer element 49 to be used alone as a bracing support. The hook-receivable material may be any type of hook-receivable material known to one skilled in the art.

The spacer element 49 may allow for the hook-receivable material to effectively form the seam 96 in FIG. 32B, so as to cover the edges of the core. Examples of hook-receivable are well known to those skilled in the art, and include materials such as broken and unbroken loop material.

FIG. 32C also exemplifies how the frictional layer 92 may include first areas 93 that have greater thicknesses than other (i.e., second, third, etc.) areas. These first areas 93 may have variable thicknesses when it is desired that there is greater cushioning or frictional support, as demonstrated by FIG. 32C by the gradually thicker first areas 93 towards the middle portion of the substrate. Further, such variable thicknesses may be advantageous in embodiments that do not include an apertured substrate, or a substrate that does not include nor has only minimal cushioning properties. As such, the thicker first areas 93 may be adapted so as to provide both the required frictional resistance and cushioning or suspension of the substrate against an object (as in the anatomy of the wearer of the substrate).

It will be noted that the frictional layer may include at least two layers of its own. For example, a top area (or layer) 103 may be a softer or compressible silicone composition, whereas the base first area (or layer) 93 may be more rigid and less compressible. This allows for the adaptation of the frictional feature to be tailored to certain anatomy that may be more distressed or sensitive, and further vary in softness across its pattern which may correspond to certain regions of the substrate upon which it is applied. An example of using and forming different layers of silicone compositions is found in U.S. Pat. No. 6,136,039, which is owned by the assignee of this disclosure and is incorporated herein by reference.

FIG. 32C also exemplifies another feature of the frictional layer in that the cross-section of the layer may vary as shown by the rounded edges 105. This configuration provides a transition of the frictional layer across the skin, thereby easing the application to and removal from skin. The rounded edges 105 may also allow the frictional layer to compress and deform without occluding any or some of the openings or ventilation of the core or other substrate. The rounded edges 105 may also provide aesthetic attributes allowing for both ornamental and functional patterns of the frictional layer. The rounded edges 105 may be formed during the normal course of forming the frictional layer.

Figure 32D:
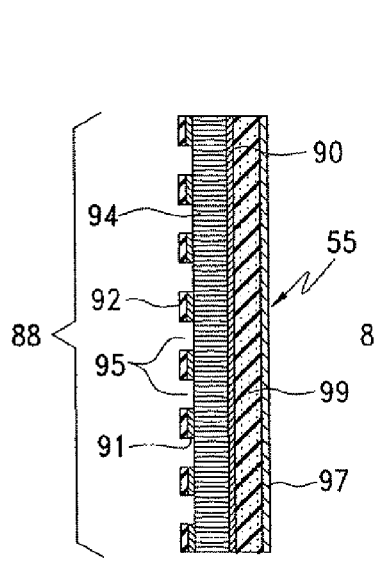
FIG. 32D is a sectional view of another variation of a spacer element.

In another spacer element variation shown in FIG. 32D, the spacer element 55 includes a foam layer 99 secured to the second surface 90 of the core 94. This foam layer 99 preferably has greater rigidity than the core 94, and is ventilated and compressible as in the core 94. A hook-receivable layer 97 may be secured to a surface of the foam layer 99.

Figure 32E:
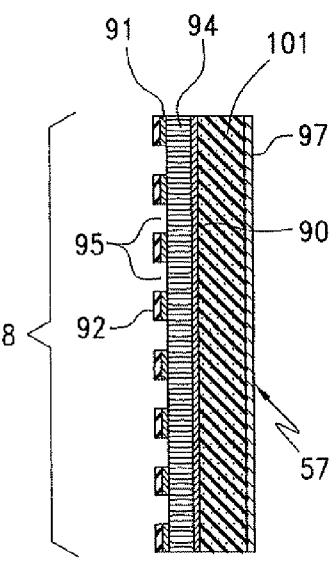
FIG. 32E is a sectional view of another variation of a spacer element.

In another spacer element variation shown in FIG. 32E, the spacer element 57 includes a thicker foam layer 101 than the foam layer 99 used in the spacer element 55. The thicker foam layer 101, while adding to the overall thickness of the spacer element, prevents shifting or wiggling of the spacer element 55. In other words, it makes the spacer element 57 more rigid. Again, as in the foam layer 99, the foam layer 101 is ventilated and compressible.

Figure 32F:
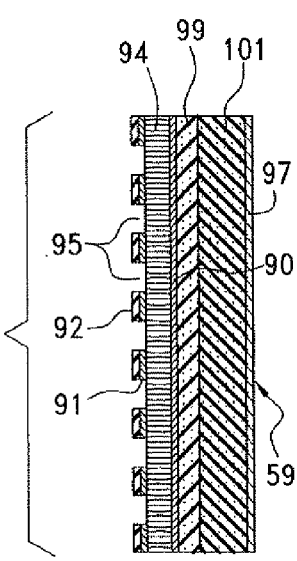
FIG. 32F is a sectional view of another variation of a spacer element.

In another spacer element variation shown in FIG. 32F, the spacer element 59 includes both foam layers 99 and 101. The multiple foam layers enables taking advantage of different properties of the foam, such as different rigidities, porosities, and densities. The hook-receivable material, and the foam layers 99 and 101 may be secured to the core and to each other by using a heat activated adhesive in a lamination process.

In another variation, as shown in FIG. 60, the spacer elements may be directly connected to the shells. Of course, such spacer elements may be configured so that they may be removed from the shells and reapplied without harming their structure. Fasteners such as hook and loop systems may be used to attach the spacer elements to the shells.

Preferred substrate materials that may be used to form the spacer elements include open or closed foams, neoprene, and textiles. For example, some of the materials could be disposable non-woven materials, neoprene or neoprene replacements (i.e., airprene or COOLMAX), perforated closed cell foams (ethylenes, eva cross-links or plastizote), circular knits, and stockings.

While numerous materials may be used as the spacer elements, according to certain embodiments it is desirable that these materials have a three-dimensional knit structure covered by a mesh that provides sufficient breathability, insulation, compression, durability, and recovery. An exemplary material is produced by Gehring Textiles under product numbers SHR 701, SHR 714 or SHR 754F.

According to this embodiment, the posterior surfaces of the spacer elements are coated with the frictional layer which comprises a continuous, discrete layer of cured silicone elastomer material 92. The silicone elastomer material is preferably sufficiently thick and soft to be comfortable to the user, and yet provides a seal between the proximal and distal members, and the skin or clothing of a user of the brace 10.

As exemplified in FIG. 32B, the silicone layer preferably has apertures which correspond to apertures of the mesh surface of the three-dimensional fabric when such a fabric is used to form the substrate of the spacer elements. In a variation, the friction feature may comprise a plurality of silicone-based dots, lines or other patterned arrangements which are deposited to the surface of the substrate of the spacer elements.

An advantage of using silicone as the frictional layer is that it may be molded to accommodate a variety of different substrates, either apertured or non-apertured. The pattern of the silicone frictional layer may be molded to correspond to irregular apertured configurations, whether they are slots, circles, squares, and other shapes, and possess varying alternatives. Moreover, the silicone frictional layer may be bonded, or directly laminated or coated onto substrates thereby providing substantial manufacturing flexibility for various substrates upon which the frictional layer is provided.

The silicone material may be mixed with scenting, anti-inflammatory, anti-bacterial, and coloring agents. Moreover, the silicone material may include skin friendly agents such as aloe vera or Vaseline. A more complete description of additives to the silicone may be found in U.S. Pat. No. 6,485,776 assigned to the assignee of this disclosure and incorporated herein by reference.

The silicone material preferably has a Shore hardness of 25-70; a minimum tensile strength of 230 lbs/inch; a 100% modulus of 8 psi; a 500% modulus of 61 psi; a minimum tear strength of 49 lbs/inch; a maximum strength of 500 lbs/inch and an elongation of about 1000%. The silicone material may be disposed in a uniform thickness in both circumferential and longitudinal directions, or may have a varying thickness to accommodate varying shapes of a body portion, protrusions, contours, etc.

It will be understood that a silicone-based frictional layer is provided as merely an example of a frictional layer. Other types of frictional layers may be provided such as those based on thermoplastic elastomers or rubbers such as styrenic block copolymers, thermoplastic polyolefins, thermoplastic vulcanisates, themoplastic polyurethanes, thermoplastic copolyesters, melt processable rubbers, and thermoplastic polyether block amides. Further, it is considered within the scope of the invention to use expanded polyester foams formed of a web-like pattern as the frictional feature.

Many of the aforementioned materials may be shaped into appropriate webs or layers that may be bonded, laminated or coated onto a substrate in order to provide a frictional feature. Moreover, as described in connection with the embodiment shown in FIG. 32C, these frictional features formed from these materials may be formed so as to have areas of varying thickness or of a thickness that are sufficient to eliminate or minimize the need for a padded substrate.

While the spacer elements are preferably shown with a frictional feature provided on their posterior surfaces, the anterior surfaces of the spacer elements may likewise be coated so as to frictionally couple with the sleeve. In the alternative, the spacer elements may be constructed of sections of elasticized fabric and coated with silicone of the type described in U.S. Pat. No. 6,592,539.

In a variation of the brace, the brace does not include the spacer elements and instead relies on the proximal and distal member straps for attachment to a user. In another variation, the spacer elements are not coated with silicone. These spacer elements provide a compressive buffer between the proximal and distal members and a leg of a user of the brace. In yet another variation, the substrate may comprise a textile having superior frictional properties, and as a result, merely the compression of the textile is sufficient to prevent rotation of the brace when worn on a leg.

In yet another variation, the spacer elements may comprise a silicone mesh comprising a textile that is impregnated with silicone. This silicone mesh defines a pattern of apertures that permit the transport of air therethrough. In yet another variation, the spacer elements form a silicone sheet having a pattern of apertures, and sufficient thickness to serve as a buffer between the sleeve, frame members, and a leg.

As with any of the spacer element embodiments and variations described herein, these spacer elements may be used in a variety of orthopedic and prosthetic applications where frictional control, breathability, compression or padding is required or desirable. The spacer elements may be used in combination with any sort of bracing or frame members, or may be used alone with or without strap or securing means.

The embodiments and variations thereof of the spacer element described herein may be used in a variety of applications in addition to those related to orthopedic and prosthetic uses. For example, the spacer elements may be adapted for use in protective gear wherein there is a need for devices that enhance suspension, rotation-resistance and breathability. Also, the spacer element may be used in intimate apparel to provide breathability, comfort and suspension. A layer of the frictional feature may be applied to gloves for additional grip. Foot apparel so as to provide ventilated and frictional means to prevent shoe slippage and to further enhance comfort. Other applications not mentioned above and requiring comfort, breathability and resistance to rotation or movement are considered to be embraced by the spacer element of this disclosure.

vii. Tightening Device

Turning to another component of the brace, the brace includes a tightening device 22, 23 that is provided for adjusting the tension of the force straps 18, 20. FIG. 33 schematically illustrates one embodiment of the tightening device as a ratcheting system 98 that permits tightening and release of a cable 102 connected to the force straps 18, 20. An end of the force strap 20 is secured to a ring 100 that is fixed to the cable 102. The tightening device 32 is configured to incrementally provide or release tension to the cord 30.

According to this embodiment, the cable 102, ring 100 and end of the force strap 20 are contained within the sleeve 12. It will be understood that in alternative embodiments, the cable, ring and force strap may be at least partially or completely outside the sleeve.

FIG. 34 illustrates an embodiment of a ratchet assembly 98 connected to the cable 102 and the ring 100. In this embodiment, the cable 102 departs from a ratchet body 106 through opening 116 and secures at one end to a seat 104 defined on the ring 100. The ratchet assembly 98 includes a rotatable handle 108 that is indexed to indicia 110 defined on the body 106. A button 112 is slidable within slot 114 and permits release of the ratchet assembly. According to this embodiment, the handle 108 rotates as the cable 102 is unwound from the ratchet assembly 98.

The handle 108 provides mechanical leverage and provides independent use and adjustable security. The indicia 110 enable a user to measure and control the degree of rotation of the handle 108, and thus determine the extent of the force applied on the knee by the force strap. The handle 108 is pivotable so as to place the ratchet assembly 98 in a low profile configuration when the handle 108 is not in use.

The internal mechanism of the ratchet assembly 98 is shown in FIG. 35. In this embodiment, the body 106 contains a ratchet wheel 126 having a plurality of teeth, and a spool 127 which are mounted to rotate together on axle 128. A pawl 118 is mounted on axle 124, and has first and second portions 120, 122 extending from the axle 124. The first portion 120 connects to the button 112, and the second portion 122 extends obliquely relative to the first portion 120 and engages teeth of the ratchet wheel 126.

FIG. 36 depicts another embodiment of the tightening device that may be used in the knee brace. According to this embodiment, a ladder strap 130 has a buckle 138 which secures to an end of the strap 20. A lever 136 is pivotably secured to the shell 40 and engages one of numerous grooves 134 of the ladder strap 130. The grooves 134 may be provided with indicia that correlate to a degree of tensioning of the strap 20 against the knee.

Preferably, the lever 136 is biased towards the ladder strap 130. A first end of the lever 136 engages one of the grooves 134 of the ladder strap 130 and secures the ladder strap 130 from movement relative to the shell 40. Of course, if pressed at a second end opposite the first end, the lever 136 is released from one of the grooves 134 and the ladder strap 130 may be adjusted relative to the lever 136 accordingly.

In this embodiment, the ladder strap 130 includes a grasping element 132 in the form of a ring formed at an end opposite the connection to the strap 20. As better exemplified in FIGS. 7 and 8, the grasping element 132 is intended to extend outwardly from the sleeve 12 so as to provide access to a user of the brace. Moreover, the latch 136 may extend outwardly from the sleeve 12 so as to facilitate adjustment of the ladder strap 130 and to permit an indication as to which groove 132 the lever 136 engages.

The ladder strap is preferably formed from a resilient material and may flex to have a curvature that generally corresponds to a leg of a wearer of the brace. The grasping element is not limited to a ring, and may be formed or comprise a variety of known constructions that permit easy handling for a user of the device. While the grooves of the ladder strap are shown as having a generally oval shape, it will be appreciated that other shapes or configurations are possible such as saw tooth teeth, rectangular teeth, and symmetrically triangular teeth.

According to one variation, the latch has a protruding forward end oriented with a bias towards the groove of the ladder strap in order to improve the latch's ability to positively engage one of the grooves of the ladder strap. The protruding forward end is preferably sized and configured to engage each of the grooves on the ladder strap.

The latch body may be pivotable between an engaged position wherein the forward end of the lever engages the grooves of the ladder strap, and a return position wherein the forward end of the lever is slidable over the grooves. In the engaged position, the protruding portion of the forward end of the latch functions as a pawl for the ladder strap. An internal biasing mechanism, such as a torsional spring, may be used to bias the protruding portion of the forward end towards the engaged position. The lever may have portions that are cutout, which not only lighten the lever by reducing the amount of material required, but also provides access to the area underneath the lever.

According to a variation of the tightening device of FIG. 36, FIGS. 37-40 illustrate a ladder strap compliant mechanism 500. In this mechanism, the latch 504 is resiliently biased towards the ladder strap 502.

The latch 504 defines opposed arms 522 which form part of an upper mount 512 that is secured to a lower mount 514 positioned on a base 506. The arms 522 are sufficiently compliant to withstand torsion in the event a rear end 526 is depressed to disengage a detent 516 located at a front end 524 of the latch 504 from the teeth 510 of the strap 502.

The ladder strap 502 defines a grasping element 508 defined at a forward end and a plurality of teeth 510 which permit incremental adjustment of a force strap. The strap 502 also defines a rear end 520 that flares in width. The latch 504 is positioned relative to the strap 502 so that the latch lies between the grasping element 508 and the rear end 520. This is so as to prevent the rear end 520 from passing through the latch 504 and to establish a maximum distance that the grasping element 508 may be drawn from the detent 516.

The base 506 is provided for mounting the latch 504 and for which the strap 502 slides thereon. The base 506 includes apertures 518 for mounting onto shells of the knee brace.

The tightening device 500 may be constructed from a variety of flexible and resilient materials including plastics, metals and composites. Moreover, the strap 502, latch 504 and base 506 may be constructed from different materials.

In a variation of the base 506 according to FIGS. 37-40, FIGS. 41-43 illustrate another base 528 having additional features to those of base 506. According to this variation, the base 528 is integrally formed with arms 530 that in turn are integrally formed to the latch 529. As with the embodiment of FIGS. 37-40, the latch 529 is resiliently biased towards the base 528, and includes detent 516.

The base 528 includes guard portions 534 that extend along the edges of the base 528 from the arms 530. These guard portions act to prevent a ladder strap from shifting laterally with respect to the detent 516.

The latch 529 includes a dosage meter 532 that indicates the relative position of a ladder strap to the base 528. The latch may also include indicia 537 that indicate a release button 536 which protrudes from the latch 529.

The base 528 includes a compliant edge 531 provided about the periphery thereof. Methods for supporting methods for making the compliant edge include those described in U.S. Pat. Nos. 5,445,602, 5,713,837 and 6,024,712 which are incorporated herein by reference. The compliant edge provides conformity to the anatomy of a wearer of the brace in that the impact of the edges of the base 528 is lessened against the wearer of the brace.

The compliant edges are relatively thinner than the base 528 and substantially more flexible than the material forming the base. The compliant edge is formed onto the base by being molded of plastic or other flexible material in a single molding step and secured together. Also, as indicated above, a compliant edge or edge portions may be provided for the shells of the knee brace wherein the compliant edge or edge portions are provided about the periphery of the shells in order to permit the edges of the shells to conform better to the anatomy of the wearer of the brace.

Figure 41:
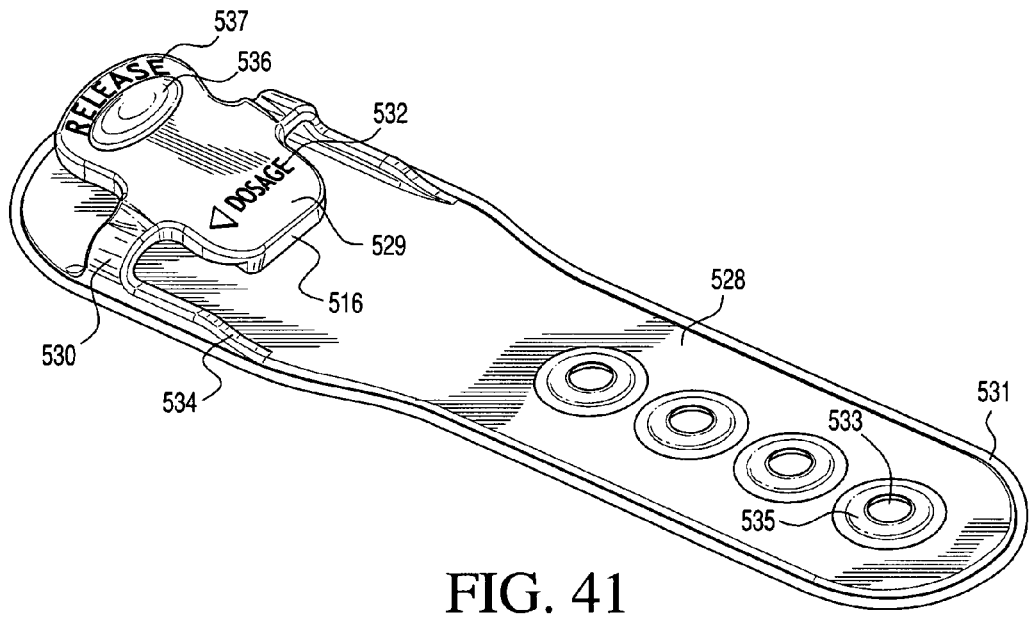
FIG. 41 is a perspective view of a variation of the base of the tightening device of FIG. 37.
Figure 42:
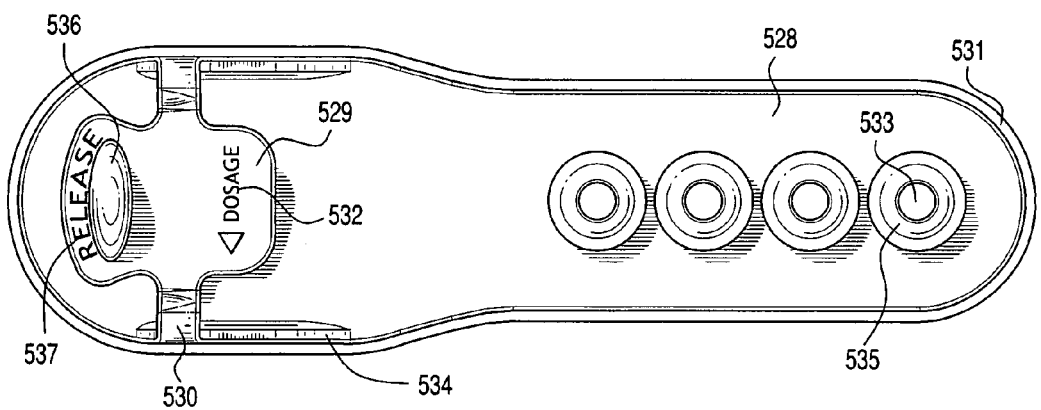
FIG. 42 is a top plan view of the base in FIG. 41.
Figure 43:
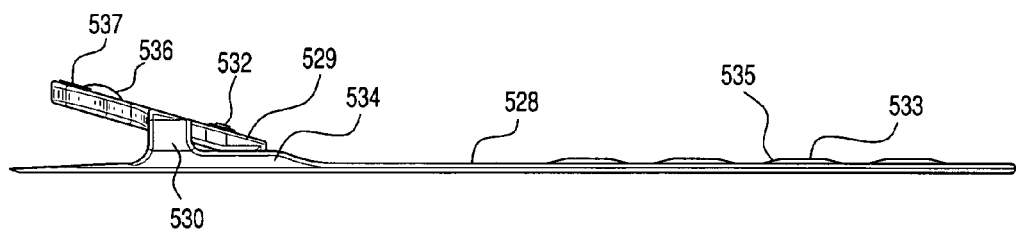
FIG. 43 is an elevational view of the base in FIG. 41.

The embodiment of the base according to FIGS. 41-43 also includes an array of holes 533 that are arranged to receive a knob (as shown in FIG. 42) for securing to the shells. Each of the holes 533 includes a rim 535 that frictionally secures against the knob. The array of holes permits the selection of placing the knob in one of the holes to effectively lengthen or shorten the distance between connection to the shells and the latch 528.

FIG. 44 illustrates the base 528 assembled with another embodiment of a ladder strap 539. In this assembly, the knob 538 is secured within one of the holes 533. The ladder strap 539 includes a plurality of indicia 542 identifying the teeth 541 of the strap 539. The ladder strap 539 also includes a plurality of apertures 543 located at an end opposite the grasping element 545. The plurality of apertures 543 are arranged to support threads, rivets or other fastening means that secure a force strap thereto.

FIG. 45 illustrates the ratchet assembly of FIG. 44 secured to the proximal shell 422 of FIG. 22. In this embodiment, the knob 538 is secured to the rim 445 of the slot 444. The security of the knob 538 with the slot 444, and hence the frame 422, allows for the tightening of a force strap 546 that is connected to the ladder strap 539 which in turn is engaging the base 528 of the ratchet assembly. As shown, the base 528 extends under the frame 422 so that the knob 538 can project through the slot 444 and secure to the rim 445.

Figure 46:
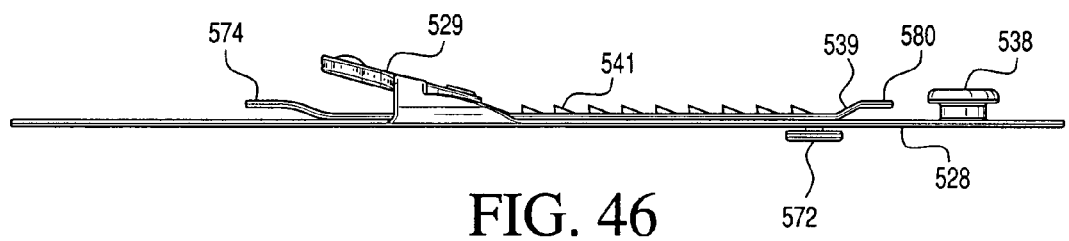
FIG. 46 is a elevational view of another variation of a tightening device.
Figure 47:
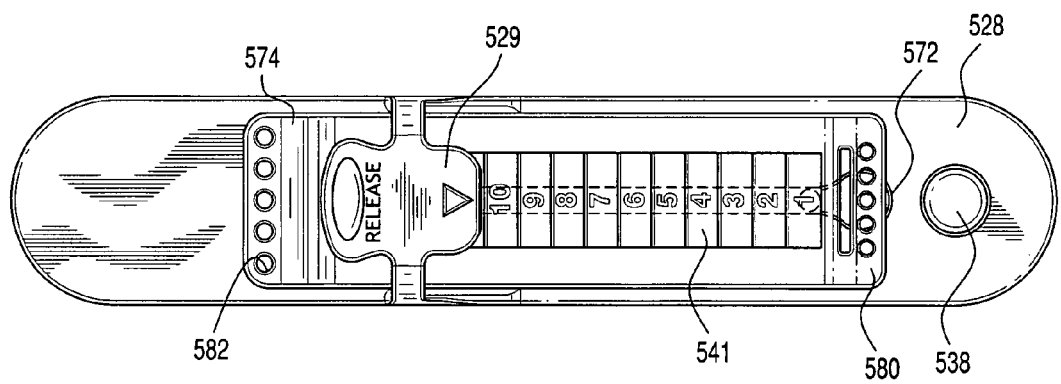
FIG. 47 is a top plan view of the tightening device according to FIG. 46.
Figure 48:
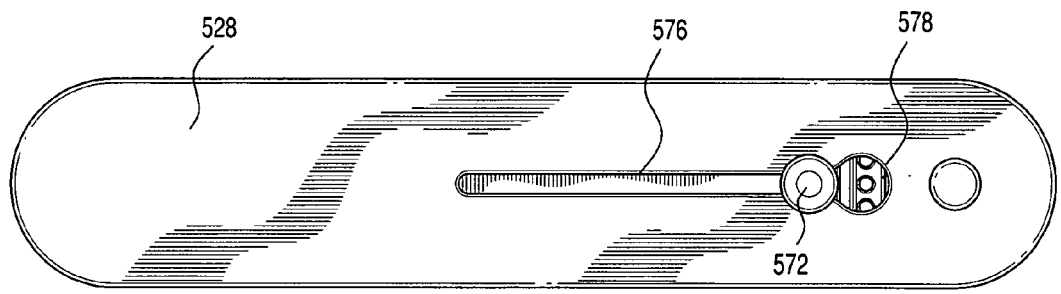
FIG. 48 is a bottom plan view of the tightening device according to FIG. 46.

FIGS. 46-48 exemplify a ratchet assembly sharing some features with the ratchet assembly of FIG. 44 and further includes a mounting system for maintaining the ladder strap 539 close to the base 528. In this example, the mounting system comprises a pin and slot system such that the ladder strap 539 forms a pin 572 that extends through a slot 576 longitudinally formed along the base 528 and a perforated tab 580. The pin 572 includes a flanged portion that is sized larger than the slot 576 and is adapted to fit through opening 578 disposed at a forward end of the slot.

The ladder strap 539 also includes a raised portion 574 with suitable apertures 582 for mounting to a force strap. This arrangement is advantageous in that the strap may be mounted generally parallel with the teeth 541 of the ladder strap 539 so as to align the forces and provide greater stability.

The mounting system is particularly provided for assuring that the ladder strap 539 remain in close proximity to the base 528 and facilitate the ratcheting thereof. This is of particular benefit in the event that the base is custom molded to conform to the leg of a patient when the ladder strap is not molded. Of course, this embodiment is merely exemplary of a mounting system and other mounting systems may also be used to effectively stabilize the ladder strap relative to the base, and hence the leg of a knee brace wearer.

Figure 49:
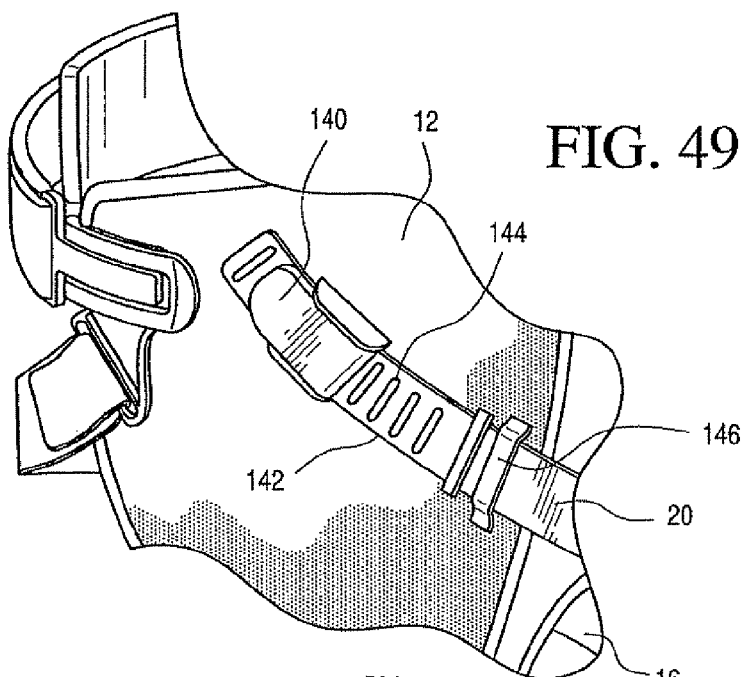
FIG. 49 is a perspective view of yet another variation of a tightening device in an embodiment of the knee brace.

FIG. 49 shows another variation of a tightening device that may use in the knee brace of this application. According to this embodiment, the force strap 20 is mounted outside the sleeve 12 or onto a frame member, and the force strap is secured to a bracket 146 at an end thereof which is connected to a ladder-type strap 142. The ladder strap 142 defines a plurality of transverse teeth or protrusions 144. A latch 140 is mounted to the sleeve 12 or a frame member in a manner similar to the embodiment of FIG. 36, which engages the teeth 144. While this embodiment does not show indicia for each position the strap is tightened relative to the sleeve 12, the teeth may be shortened and have a width that is less than the width of the ladder strap 142. Indicia may be provided alongside each tooth of the ladder strap.

According to yet another variation, loop material is secured onto a strap and hook material is secured onto a corresponding shell. Alternatively, a plurality of rings are provided on the shells through which the force straps pass through. The force straps include hook and loop portions that correspond to one another and permit maintaining the force straps in place.

Commercial examples of a tightening device that may also be used with different embodiments of the knee brace include the BOA lacing system of BOA Technology Inc. of Steamboat Springs, Colo., or in the alternative a ratcheting buckle in combination with a ladder strap that is sold by M2 Inc. of Winooski, Vt. under product name 1" Mechanical Closure System (part numbers RB502 & LS 118-WB).

in any of the embodiments concerning the tightening device, it is intended that the tightening device provide precise adjustment, whether incremental or not of the force strap, and possess a sufficiently robust construction to withstand the tensile stress of the force straps. Different configurations of hook and loop fastener systems, buckles, straps, cords and ratchets are clearly envisioned as being used in the tightening device so as to provide simple adjustment and effective adjustment of the force straps.

In any of the embodiments concerning the tightening device, it is intended that the tightening device provide precise adjustment, whether incremental or not, of the force strap, and possess a sufficiently robust construction to withstand the tensile stress of the force strap. Different configurations of hook and loop fastener systems, buckles, straps, cords and ratchets are clearly envisioned as being used in the tightening device so as to provide simple adjustment and effective adjustment of the force straps.

viii. Strap Attachment Piece

Figure 50:
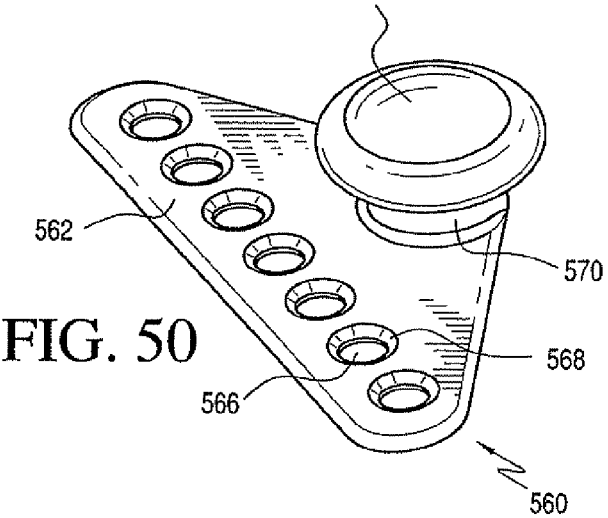
FIGS. 50-52 show an embodiment of a strap attachment piece.
Figure 51:
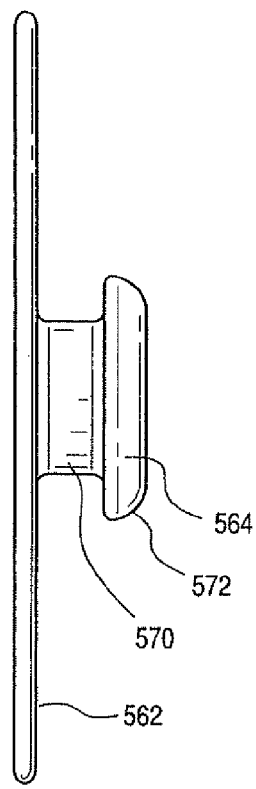
Figure 52:
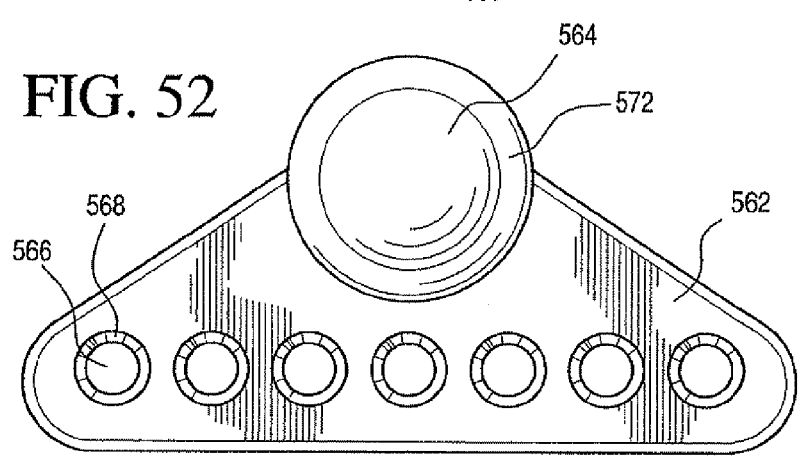

An embodiment of a strap attachment piece 560 is shown in FIGS. 50-52. According to this embodiment, the piece 560 includes a generally triangular body 562 forming a neck 570 having a knob 564 that is formed at a first end of the body 562. The knob 564 includes a tapered head portion 572 that facilitates securing the knob 564 onto one of the slots of the frame members, for example slot 446 of FIG. 22.

A plurality of apertures 566 are defined between second and third ends of the body 562. Each of the apertures 566 includes a tapering portion 568 beginning from the side of the body 562 including the knob 564 to preferably the opposed side of the body 562. The tapering portion 568 eases the pressure exerted onto body 562 by stitching, rivets, pins or other suitable means useable for securing straps to the piece 560.

Figure 8:
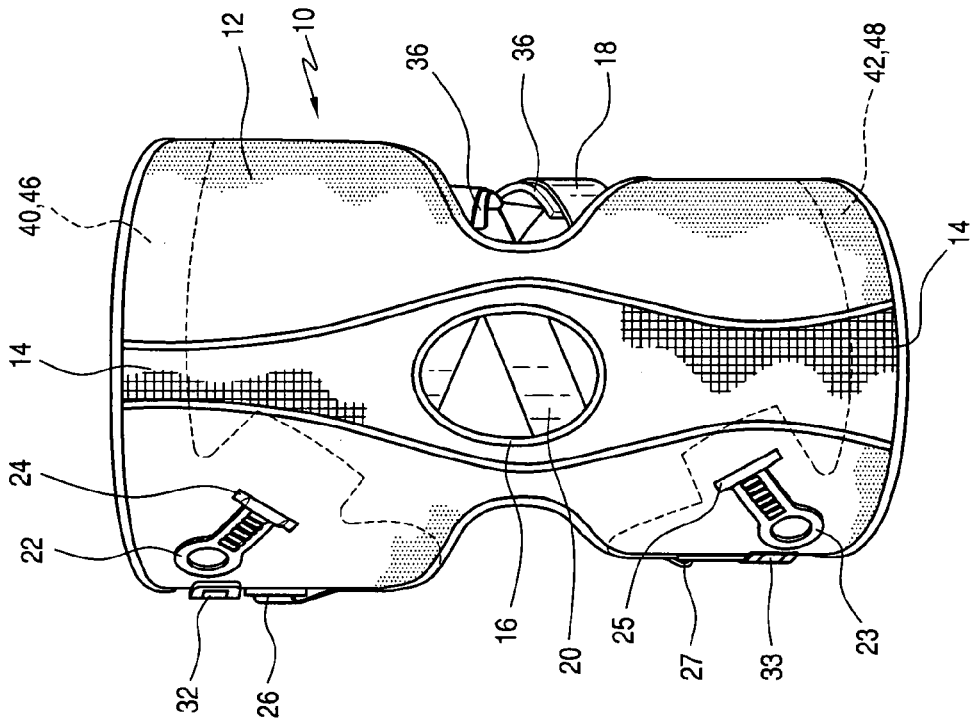
FIG. 8 is a front elevation view of the embodiment of FIG. 7.

Referring back to the brace in FIGS. 7 and 8, the brace includes the buckle assemblies 32, 33 that connect to the stability straps 28, 30. It is preferred that the buckle assemblies 32, 33 generally have a low profile so that they do not protrude greatly from the sleeve. Moreover, the buckle assemblies should be relatively simple to use while having an anatomically conforming shape and providing sufficient leverage to tightly secure the stability straps against the leg.

ix. Buckle Assembly

Figure 53:
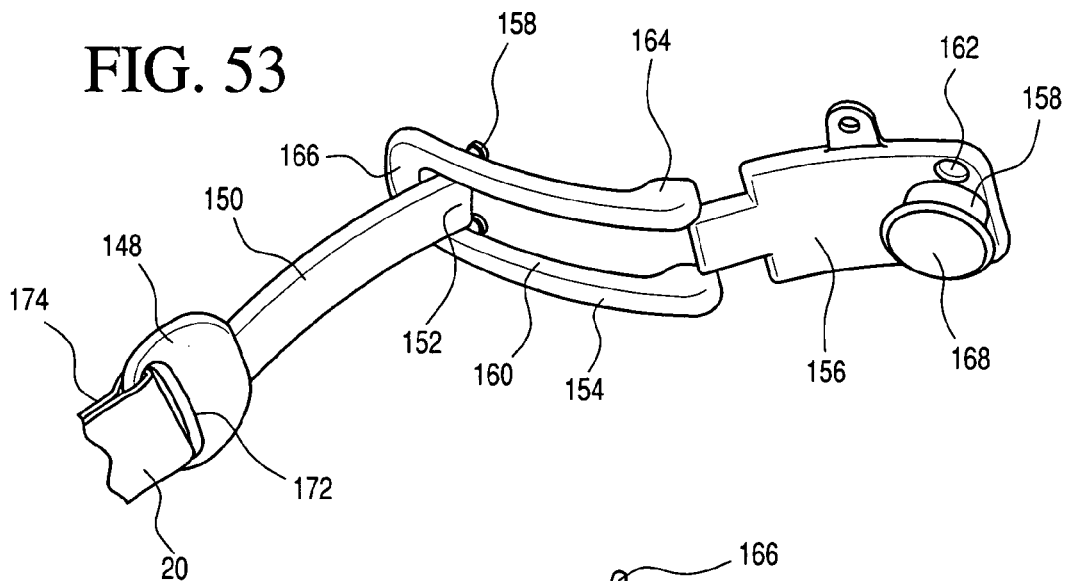
FIGS. 53-55 are perspective views of a variation of a buckle assembly of the knee brace.
Figure 54:
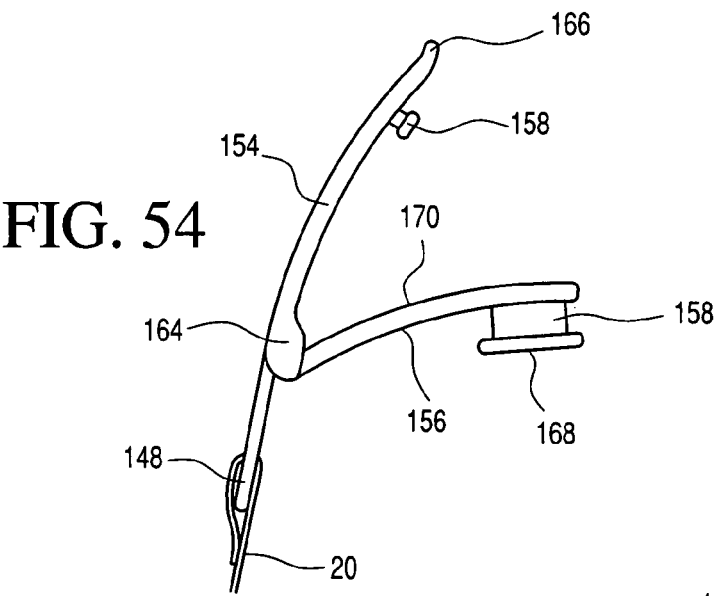
Figure 55:
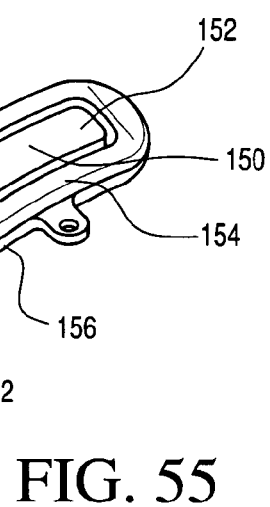

In an embodiment of the buckle assembly shown in FIGS. 53-55, a low profile buckle assembly is provided which locks the stability straps 28, 30 in position relative to the shells 40, 42. This embodiment includes bracket 148 that secures to the strap 20 and connects to an arm 150 having a forward end 152 slidably engaging a lever body 154. The arm 150 extends through a clearance 160 defined by the lever element 154 and has protruding elements 158 that engage with edges of the lever body 154 defining the clearance 160 that extends from a forward end 166 to a rearward end 164 of the lever body 154. As a result of the construction of the lever body 154, and its relationship to the arm 150, the arm 150 is slidably connected to the lever body 154.

A base element 156 is pivotably connected to the rearward end 164 of the lever body 154. The base element 156 includes receiving holes 162 that are configured to receive the protruding elements 158 of the arm 150, and a locking feature 158 for securing onto one of the shells 40, 42. According to this embodiment, the locking feature is a button body having a head portion 168 with a diameter greater than the rest of the button body. The head portion 168 is intended to have a diameter greater than the seat portion 64 of the eyelet 62 defined on the shells 40, 42.

The lever element 154 is pivotable between a disengaged position shown in FIG. 53 and an engaged position shown in FIG. 55. FIG. 54 shows an intermediate position between the disengaged and engaged positions. In the engaged position, the forward end 164 of the lever element 154 is brought against surface 170 of the base element 156, and the arm 150 rests upon the surface 170 with the protruding elements 158 engaged with the receiving holes 162 of the base element 156.

Preferably, the protruding elements 158 are resiliently urged into the receiving holes 162. In the disengaged position, the lever body 154 is pivoted away from the surface 170 of the base element and the protruding elements 158 are removed from the receiving holes 162. The arm 150 may be positioned between the forward end 166 and rearward end 164 of the lever body 154, and a pin (not shown) may be located at the connection.

The bracket 148 includes a ring 172 for the strap 20 to extend through. In this embodiment, the strap 20 has a hook and loop system permitting an end portion 174 of the strap 20 to secure to a receiving portion 176 of the strap 20. A user may set an approximate desired length of the strap using the hook and loop system prior to securing the buckle assembly. Subsequently, the buckle assembly is placed in the engaged position so as to securely place and secure the knee brace on the leg.

The buckle assembly includes a curved profile such that it conforms to the leg of a wearer of the brace. This imparts a more streamlined buckle assembly and further prevents buckle assembly from snagging on clothing or acting as an impediment to the wearer of the brace.

Another variation of a buckle assembly 188 is depicted in FIGS. 56-58. In this variation, the base element 193 and the bracket body 191 are connected to one another, thereby reducing the amount of parts and simplifying donning of the bracket and buckle to the shells.

As with other variations of the bracket assembly, the bracket body 191 includes a clearance 192 arranged for receiving a strap. The buckle portion of the assembly 188 is similarly arranged as in the embodiments of FIGS. 53-55 in that it includes common features such as the base element 189, lever body 190, arm 193, protruding element 197, and bracket 191 having the clearance 192.

The buckle assembly 188 has a securing feature located at the end portions of the base element 189 and the lever body 190. Specifically, the base element 189 carries a recess 199 upon which a hook 198 formed from the lever body 190 secures thereonto. The hook 198 is biased to extend into the recess 199 and urge against the base element 189. The hook 198 is also resilient so that it can deflect when the lever body 190 is urged away from the base element 189.

The buckle assembly 188 also includes a bracket 195 which extends obliquely relative to the base element 198. The bracket 195 includes a clearance 196 that is arranged to receive a force strap. The buckle assembly 188 has a curved profile that is similar to the curved profiles of the buckle assembly of FIGS. 53-55.

Figure 59:
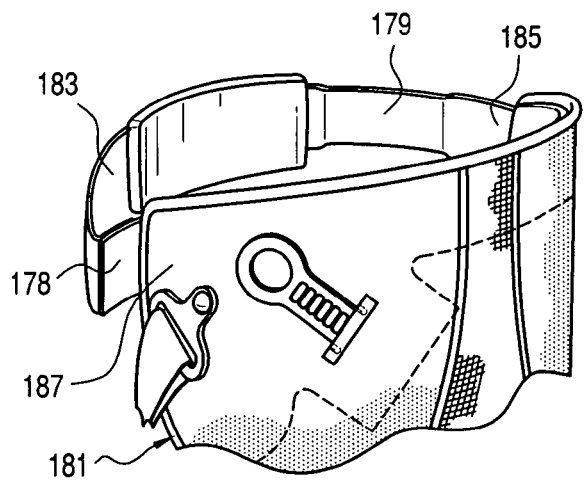
FIG. 59 is a perspective view of another variation of a buckle assembly.

In yet another variation of a buckle assembly depicted in FIG. 59, a clamping member 178 tightens the stability strap 179 to the brace 181. According to this variation, a second side 185 of the strap 179 is secured to one side of the brace 181, and a first side 183 of the strap 179 secures to the clamping member 178. The clamping member 178 is pivotally connected to the brace 181, and is arranged to be biased against an external surface 187 of the brace 181. The second side 185 of the strap 179 is detachable from the clamping member 178 and may be secured therewith with a hook and loop fastener system.

The buckle assembly may be constructed from plastic or a reinforced composite. A plastic construction provides the sufficient resiliency for the protruding elements to compliantly pass through the receiving holes of the base element. Moreover, the plastic buckle assembly reduces weight of the brace and has some compliancy against the leg of a user of the brace. It is possible to reinforce the buckle assembly with a carbon content, such as a TRIAX based buckle assembly. Other examples of composite based buckle assemblies include those constructed with delron or nylon having reinforcing carbon, KEVLAR or glass fibers.

It will be noted that the buckle assembly may also have parts that are constructed from metal, such as an aluminum or titanium alloy. The metal parts provide superior strength and may be sufficiently lightweight. In such a metal based bracket assembly, the protruding elements may be metal components having a resilient o-ring surrounding the protruding elements that has sufficient compressive properties to be placed through the receiving holes of the base portion. Of course, in such an embodiment, the metal protruding parts preferably have a diameter less than the diameter of the receiving holes.

Variations of the aforementioned buckle assembly may be used to secure the stability strap to the brace. These variations include an embodiment wherein the strap is fastened to a buckle assembly with a rivet, and a ring is provided on a side of the sleeve opposite the buckle assembly. The length of the strap may be simply adjusted with a hook and loop system provided on the strap.

In a variation of the buckle and tightening devices described above, the tightening devices may be secured to a buckle instead of being directly connected to the shells. This permits the buckle to control both ends of the straps.

In accordance with one method for donning the knee brace with the inventive buckle assembly, the method is performed in the following steps. First, one force strap is attached to a corresponding buckle assembly, thus requiring only one connection as opposed to two. Next, during an initial fitting, the buckle assembly is connected to the shell and subsequently locked. The leg of the wearer is extended and the force strap is then adjusted such that the force strap is adjustable in length. This results in removing the need to adjust the length of the force strap upon each donning unless the leg changes in size, or for some other reason. The stability strap corresponding to the buckle assembly is also tightened accordingly. Both buckle assemblies are connected to the shells, and the remaining unsecured force straps and stability straps are tightened.

Unloading of the knee is conducted with the wearer flexing the knee by bending it, and by tensioning the force strap with corresponding tightening devices. After the wearer is finished with wearing the knee brace, the force strap is released and the buckle assembly is opened. The buckle assembly is then removed from the shells, and the brace is subsequently removed.

Upon repeated use, there is no need to adjust the stability straps, and the force straps other than by the tightening device to unload the knee; all of the stability straps and force straps are already configured. Alternatively, a wearer may simply release the tension of the force straps, unbuckle the buckle assembly, and slide the knee brace off of the leg. In either way, the arrangement provides for simple donning of the knee brace onto a leg, and expedites securing and removal of the knee brace.

x. Hinge

In another feature of the knee brace, FIG. 60 schematically shows a brace 300 having a hinge 301 in combination with a force strap system of any of the aforementioned embodiments. The hinge 301 extends between frame members 309, 311.

The frame members 309, 311 include corresponding liners 349, 351, respectively.

Preferably, the hinge has flexion and extension stopping features to control hyperextension and anterior drawer of the tibia, The hinge may have an adjustment mechanism that enables a user or clinician to adjust the varus/valgus angle of the hinge.

One variation of a hinge 260 for use in the brace of FIG. 60 is shown in FIG. 61. This hinge 260 is generally constructed from plastic or reinforced composite so as to be lightweight and have a generally low profile. The hinge 260 includes flexible brackets 262 that are provided for connecting to the frame members 309, 311. A first end of the proximal and distal arms 264, 266 connect to corresponding brackets 262, A second end of these arms 264, 266 defines a head 268, 270 having a generally circular gear portion 272, 274. The heads 268, 270 are pivotably mounted about axles 276, 278 of a housing 280 such that the gear portions 272, 274 mesh with one another.

Each head 268, 270 is provided with first and second stop structures 282, 286. The first stop structures 282 are located on an anterior side of the hinge 260 and are arranged to contact a side surface 284 of the housing 280 in order to limit rotation of the hinge 260 in the anterior direction of the brace. The second stop structures 286 of the head are formed on a generally posterior side of the hinge, and are arranged to limit rotation in the posterior direction of the brace.

Apertures 288 may be formed in the housing 280 along the path of the stop structures as the heads 268, 270 rotate. These apertures are adapted to receive a screw or pin. The screw or pin is provided to block or engage one of the first and second stop structures to further limit rotation of the hinge.

Figure 62:
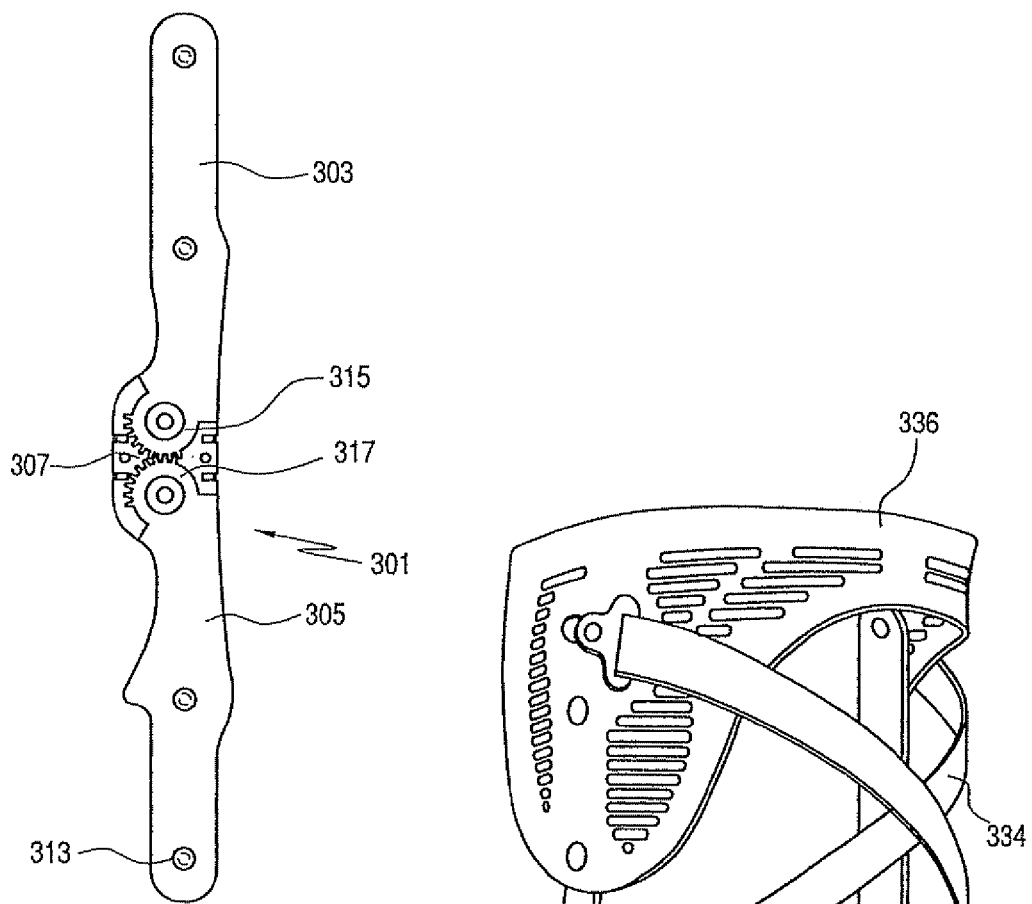
FIG. 62 is an elevational view of another variation of a hinge.

In a variation of the hinge, FIG. 62 shows a hinge 301 having a different arm construction from the construction of hinge 260. According to this variation, the arms 303, 305 are integrally formed with corresponding heads 315, 317. In addition, each of the arms 303, 305 is contoured to accommodate or correspond to the shape of the distal and proximal shells of the knee brace. Gear meshing area 307 exists between heads 315, 317.

FIG. 60 shows the hinge 301 connected to proximal and distal shells 309, 311 having liners 349, 351, respectively. In this variation, the hinge 301 includes a face plate 319 that covers the heads 315, 317. The arms 303, 305 are bent to generally anatomically accommodate a leg. Also, the arms 303, 305 are secured to respective shells via pins or buttons 313.

The hinge 301 may be releasably securable to the shells 309 and 311 in Fig. 60 via the buttons 313. The buttons 313 are configured to be insertable into the openings 321 and locked in a slotted portion (not shown) that is similar to the slots 445 in the frame 422 of FIG. 45, or other frame slots described herein.

According to other variations, the removable hinge may be secured to the shells with a series of corresponding snap fasteners, or other suitable fastener devices. The shells may be particularly configured to include apertures that can receive self-piercing fasteners. The removable hinge enables wearers to use the hinge for intense leg activity and greater stability, and remove the hinge for more normal use, greater comfort, and a more streamlined brace.

The hinge controls the motion and angular displacement of the brace for stabilization and control of the knee joint. Preferably, the hinge has a thin profile, and is constructed of a lightweight material such as plastic, composite materials, or metals. Unlike other hinges, this hinge does not include an adjustment mechanism since as soon as the force strap system 256 draws the knee against the hinge, the hinge would deflect away from the knee due to its flexibility.

Other hinge types may be employed such as those described in U.S. Pat. No. 5,277,698 currently assigned to Generation II USA, Corp. of Bothell, Wash., or in the alternative with a anatomically orthopedic hinge described in U.S. Patent Application Publications 2004/0002674 A1 and 2004/0054311 A1 assigned to Generation II USA, Corp. of Bothell, Wash. This patent and these application publications are incorporated herein by reference.

Figure 63:
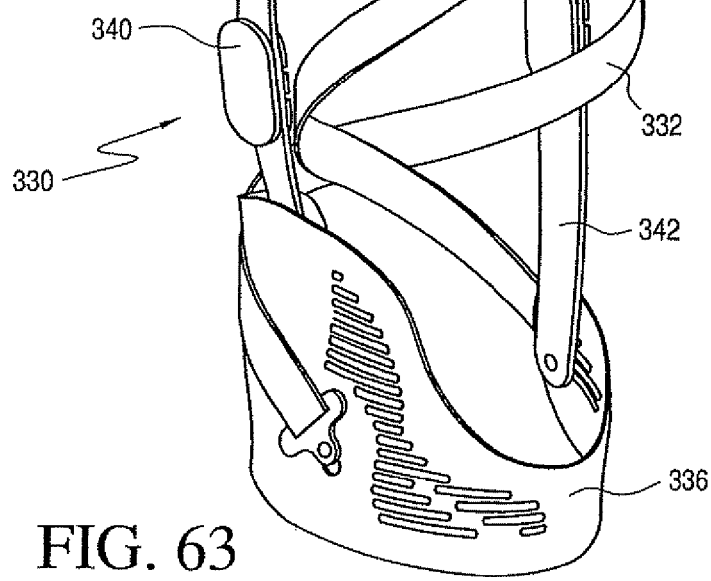
FIG. 63 is a perspective view of another embodiment of the knee brace.

Another embodiment of the knee brace 330 is shown in FIG. 63 that is configured for stabilizing both medial and lateral sides of the knee. According to this embodiment, force straps 332, 334 are configured to extend about opposite sides of the brace 330. Each of these straps 332, 334 connects to frame members 336 that may comprise any of the aforementioned variations discussed herein.

In this embodiment, the force straps 332, 334 are provided to apply equal pressure on both sides of the knee. Depending on the configuration, one force strap extends along a proximal, lateral side of the knee whereas the other force strap extends along a distal, medial side of the knee. This embodiment is particularly useful for treating ligament injuries or infirmities due to the stability it provides for the knee.

A hinge or opposed hinges 340, 342, such as the type of hinges discussed in connection with FIGS. 61 and 62, may also be employed to further stabilize the knee with this embodiment.

xi. Alternate Knee Brace Embodiment

Figure 64:
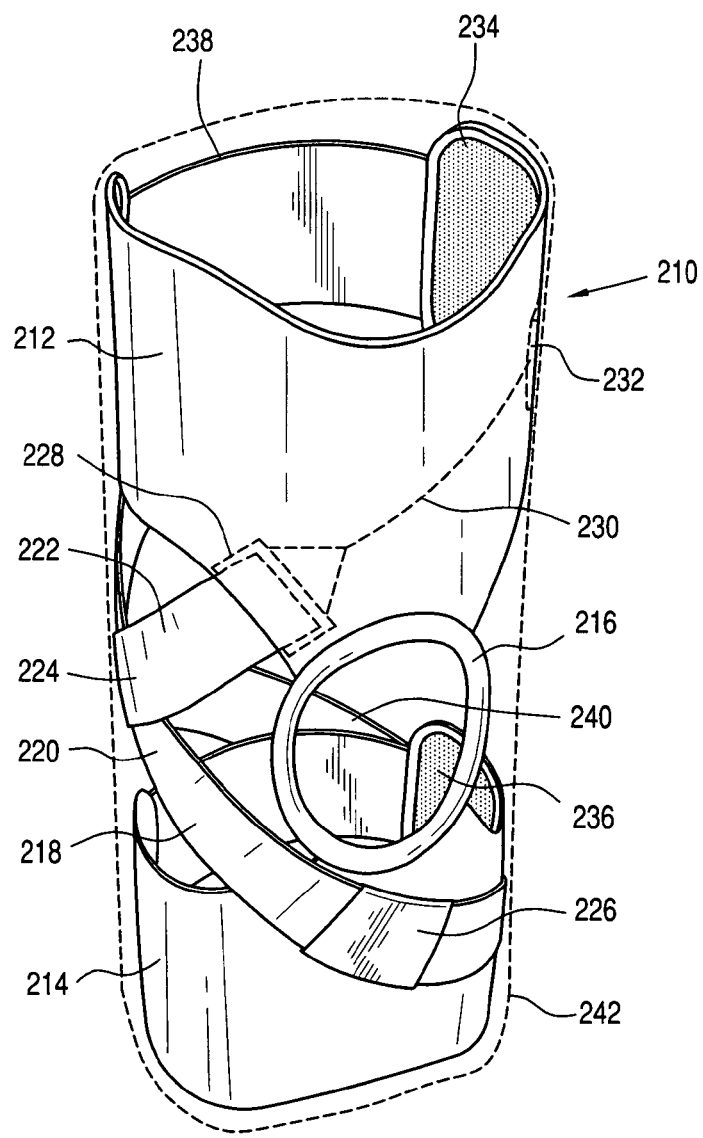
FIG. 64 is a perspective view of another embodiment of the knee brace.

FIG. 64 illustrates another embodiment of a knee brace 210 in accordance with the present invention. This brace 210 includes a proximal frame member 212 and a distal frame member 214 both located on the anterior side of the device 210, and extending between lateral and medial portions thereof. Both the frame members 212, 214 have anterior and posterior facing surfaces. A connecting element 216 connects the frame members 212, 214. A force strap 218 is connected to the frame members 212, 214, and defines first and second strap portions 220, 222 that cross at an intersection area 224 located between the frame members 212, 214.

The intersection area 224 is generally defined in the same region as in the intersection area in the embodiment of FIGS. 7-10. Moreover, the location of the force strap 218 relative to the frame members 212, 214 is similar to that also described in connection with the embodiment of FIGS. 7-10.

A first end of the first strap portion 220 is anchored to the proximal frame member 212 and spirals towards the distal frame member 214. A plurality of strap guides 226 guide the force strap 218 along an outer surface of the distal member 214 and redirect the force strap 218 towards the proximal member 212. The second strap portion 222 emerges from the distal member 214 and intersects with the first strap portion 220 while extending towards the proximal member 212.

A second end of the second strap portion 222 is secured to a bracket 228 connected to a cord 230. The cord 230 is received by a tightening device 232, of any of the types described herein that are secured to the proximal member 212. The tightening device 232, as described in connection with the aforementioned embodiments, is provided to incrementally tension the force strap 218 and selectively allow release of tension in the force strap 218. The connection between the second strap portion 222 and the tightening device 232 is oriented in a predetermined direction to obtain a preferred orientation at the intersection area 224 between the first and second strap portions 220, 222.

Proximal and distal spacer elements 234, 236 are connected to the frame members 212, 214, respectively, along the inner surfaces thereof. As with the aforementioned spacer elements, the spacer elements 234, 236 have a coating that has a high frictional coefficient against skin or clothing. When applied against skin or clothing, the friction spacer elements 234, 236 resist movement of the knee brace 10 relative to the skin or clothing.

The proximal member 212 includes a stability strap 238 secured and extending between opposed lateral and medial sides of the proximal member 212. The distal member 214 includes a stability strap 240 likewise secured and extending between opposed lateral and medial sides of the distal member 214. The proximal and distal straps 238, 240 preferably have hook and loop fastener systems to connect to the medial and lateral sides of the respective frame members 212, 214.

According to the embodiment of FIG. 64, the frame members 212, 214 may be rigid or flexible members. Moreover, they may be perforated or rendered breathable in the manner described in reference to the shells of FIGS. 18 and 19. In variations of the knee brace, however, the frame members may be constructed of soft members that are sufficiently strong to withstand forces on a knee produced by the force strap 218 but sufficiently compliant to provide comfort to a user of the knee brace.

The connecting element 216 is a ring that connects to both the proximal and distal members 212, 214. The connecting element 216 is not limited to a ring-like structure, and instead may be provided in any shape having suitable structure and strength that is sufficient to maintain the frame members 212, 214 apart while providing sufficient bending over the knee cap during gait.

The connecting element is preferably constructed of a medial grade silicone having a sufficient durometer (i.e., 10) and sufficient stiffness to maintain the frame members 212, 214 apart. Alternatively, the connecting element 216 may be constructed of a stiff foam from EVA, plastezote or polyurethane.

In a variation at least one hinge provided on one of the medial or lateral sides of the brace may take the place of the connecting element, or be provided in combination with the connecting element.

The tightening device 232 may include any one of the aforementioned systems used for tightening the force strap 218. Moreover, the force strap 218 and the stability straps 232 may be mounted onto the shells in any of the aforementioned manners described in connection with the embodiment of FIGS. 7-10.

xii. Additional Features

Additional features may be used in connection with the aforementioned embodiments of the knee brace.

One such feature includes load cells that are connected to force straps to measure the force exerted on a knee. According to this feature, load cells are connected to the first and second force straps. These load cells monitor the pressure applied on a knee and relay via connections a pressure reading to the tightening device. The tightening device according to this embodiment, is equipped with a drive motor (not shown) that incrementally adjusts the tightening device by either tightening or releasing the force straps.

Of course, this embodiment is not limited to requiring two load cells, and one or multiple load cells may be used to determine the pressure on the knee caused by the force strap.

This feature of the tightening device is particularly advantageous since it permits precise tension adjustment of the strap to treat a specific user. The predetermined parameters include a range of dosage requirements for users. These dosage requirements include forces required for a user to unload the compartmental osteoarthritis of the knee. For example, one dosage would equal about 3 Nm of unloading. The maximum unloading, in this example, is 12 Nm so 4 doses would provide a maximum unloading of the knee. The load cells may be configured for a user during a fitting process by an orthotist who could establish a dosage requirement for the user.

In another variation, the load cells may be integrated with the knee brace and the tightening device. The data obtained by the load cells can then be used by the tightening device to change the tension in the force strap during a gait cycle. According to this variation, an accelerometer device is required to determine the stage of the gait at a particular point in time. This can be particularly useful when walking up or down ramps or hills, or going up or down stairs since the knee is bears weight when in flexion so that the strap is pulled tighter during such stages of walking.

In another feature that may be used in combination with embodiments of the knee brace, an inflatable bladder system for providing additional cushioning and fitting of the force straps and stability straps. As illustrated, the force straps are provided with a plurality of bladders connected to pump to provide relief to a leg. The bladders are particularly positioned on the force straps at locations proximal and distal of the leg whereat the force straps apply the maximum pressure on the knee.

In operation, the force straps are applied over the knee with slight tension. As the bladders are inflated, the force straps tighten over the knee due to the increase in size of the bladders. The pump permits inflation and deflation of the bladders. The pump may be integrated with the force straps or be located remote therefrom.

Examples of pump and bladder systems that may be used in combination with the force strap of the knee brace are described in U.S. Pat. Nos. 5,022,109 and 6,598,250 assigned to Dielectrics Industries of Chicopee, Mass., which are incorporated herein by reference.

The various embodiments of knee braces described above in accordance with present invention thus provide a product that reduces pain, speeds a healing process, and imparts improved stability to the knee. The knee brace is lightweight and has a streamlined profile that is simple to use for wearers of the brace of various age groups. Moreover, the knee brace permits more precise adjustment of the brace and enables efficient coordination between a medical professional and the wearer as to the degree the knee brace should be configured. Patient comfort is also enhanced, and donning and doffing of the brace is eased with the novel features of the present knee brace.

Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments. In addition to the variations described herein, other known equivalents for each feature can be mixed and matched by one of ordinary skill in this art to construct a knee brace in accordance with principles of the present invention.

Although this invention has been disclosed in the context of certain preferred embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An orthotic or prosthetic spacer element, comprising:
   a three-dimensional knit fabric having first and second surface layers spaced by a ventilated and compressible core, the first surface layer being a fabric mesh forming a plurality of uniformly spaced apertures arranged in a pattern and having a predetermined shape;
   a discrete and continuous frictional layer defined as a sheet of silicone elastomer laminated onto the first surface layer, the frictional layer having a plurality of apertures arranged in a pattern, the pattern of the frictional layer apertures are in direct correspondence to the pattern of the first surface layer apertures, the apertures of the frictional layer having the same shape as the apertures formed by the first surface layer, wherein the apertures of the frictional layer open over the ventilated core and are formed independently from the core;
   wherein the frictional layer extends continuously over the first surface layer in areas outside of the apertures formed by the first surface layer.

2. The spacer element according to claim 1, further comprising:
   a first compressible material layer secured to the second surface layer, wherein the first compressible material layer is generally more rigid than the core.

3. The spacer element according to claim 2, further comprising a second compressible material layer secured to the first compressible material layer, the second compressible material layer having a different rigidity from the rigidity of the first compressible material layer.

4. The spacer element according to claim 3, wherein the second compressible material layer is thicker than the first compressible layer.

5. The spacer element according to claim 2, wherein the first compressible material layer has a thickness greater than a thickness of the core.

6. The spacer element according to claim 1, further comprising:
   a compressible material layer having opposed first and second surfaces, the compressible material layer first surface connected to and generally parallel with the second surface layer.

7. The spacer element according to claim 6, wherein the compressible material layer is generally more rigid than the core.

8. The spacer element according to claim 6, further comprising:
   a hook-receivable backing layer secured to the compressible layer second surface.

9. The spacer element according to claim 1, further comprising:
   a hook-receivable textile-based backing layer having first and second opposed surfaces, the backing layer first surface secured to the second surface layer.

10. The spacer element according to claim 9, further comprising:
    peripheral edges formed from the hook-receivable backing layer generally extending about the periphery of the spacer element.

11. The spacer element according to claim 1, further comprising:
    a hook-receivable backing layer secured to the core second surface.

12. The spacer element according to claim 1, wherein the frictional layer has greater frictional properties than the first surface layer.

13. The spacer element according to claim 1, wherein the sheet of silicone elastomer has a shore hardness of 25-70.

14. The spacer element according to claim 1, wherein the sheet of silicone elastomer has a substantially uniform thickness.

15. The spacer element according to claim 1, wherein the sheet of silicone elastomer has a minimum tensile strength of 230 lbs/inch.

16. The spacer element according to claim 1, wherein the frictional layer has a high frictional coefficient against skin or clothing.

17. The spacer element according to claim 1, wherein the corresponding pattern of apertures of the first surface layer and the frictional layer are arranged in alternating rows, the apertures being formed as elongate slots.

18. The spacer element according to claim 1, wherein the fabric mesh of the first surface layer is a textile and the silicone of the frictional layer impregnates the textile of the fabric mesh.

19. A ventilated orthotic or prosthetic spacer element, comprising:
- a three-dimensional knit fabric having first and second surface layers spaced by a ventilated and compressible core, the first surface layer being a fabric mesh forming a plurality of uniformly spaced apertures arranged in a pattern and having a predetermined shape;
- a discrete and continuous frictional layer defined as a sheet of silicone elastomer laminated onto the-first surface layer, the frictional layer having a plurality of apertures arranged in a pattern, the pattern of the frictional layer apertures are in direct correspondence to the pattern of the first surface layer apertures, the apertures of the frictional layer having the same shape as the apertures formed by the first surface layer, wherein the apertures of the frictional layer open over the ventilated core and are formed independently from the core;
- wherein the frictional layer impregnates the first surface layer and extends continuously over the first surface layer in areas outside of the apertures formed by the first surface layer; and
- a layer of hook-receivable material secured to the core second surface.

20. The spacer element according to claim 19, further comprising:
- a compressible material layer interposed between the three-dimensional knit fabric and the hook-receivable layer.

21. The spacer element according to claim 20, wherein the compressible material layer has greater rigidity than the three-dimensional knit fabric.

22. The spacer element according to claim 19, wherein the frictional layer has greater frictional properties than the first surface layer and the hook-receivable layer.

23. The spacer element according to claim 19, wherein the sheet of silicone elastomer has a shore hardness of 25-70.

24. The spacer element according to claim 19, wherein the sheet of silicone elastomer has a substantially uniform thickness.

25. The spacer element according to claim 19, wherein the corresponding pattern of apertures of the first surface layer and the frictional layer are arranged in alternating rows, the apertures being formed as elongate slots.

26. The spacer element according to claim 19, wherein the fabric mesh of the first surface layer is a textile and the silicone of the frictional layer impregnates the textile of the fabric mesh.

* * * * *